(12) United States Patent
Son et al.

(10) Patent No.: US 11,534,283 B2
(45) Date of Patent: Dec. 27, 2022

(54) POROUS IMPLANTABLE DEVICES

(71) Applicants: CHILDREN'S NATIONAL MEDICAL CENTER, Washington, DC (US); UNIVERSITY OF MARYLAND, COLLEGE PARK, College Park, MD (US)

(72) Inventors: Alexander I. Son, Washington, DC (US); Kazue Hashimoto-Torii, Bethesda, MD (US); Masaaki Torii, Bethesda, MD (US); Paul D. Morton, Silver Spring, MD (US); Seiji Ishii, North Bethesda, MD (US); Justin Opfermann, Washington, DC (US); Judy Liu, Washington, DC (US); John Fisher, Kensington, MD (US); Marco Santoro, Silver Spring, MD (US); Peter C.W. Kim, Washington, DC (US)

(73) Assignees: CHILDREN'S NATIONAL MEDICAL CENTER, Washington, DC (US); UNIVERSITY OF MARYLAND, COLLEGE PARK, College Park, MD (US)

( * ) Notice: Subject to any disclaimer, the term of this patent is extended or adjusted under 35 U.S.C. 154(b) by 344 days.

(21) Appl. No.: 16/645,221

(22) PCT Filed: Sep. 6, 2018

(86) PCT No.: PCT/US2018/049675
§ 371 (c)(1),
(2) Date: Mar. 6, 2020

(87) PCT Pub. No.: WO2019/051034
PCT Pub. Date: Mar. 14, 2019

(65) Prior Publication Data
US 2020/0289250 A1 Sep. 17, 2020

Related U.S. Application Data

(60) Provisional application No. 62/554,680, filed on Sep. 6, 2017.

(51) Int. Cl.
*A61F 2/02* (2006.01)
*A61L 31/04* (2006.01)
(Continued)

(52) U.S. Cl.
CPC ............ *A61F 2/0077* (2013.01); *A61F 2/022* (2013.01); *A61K 35/30* (2013.01);
(Continued)

(58) Field of Classification Search
CPC ................... A61F 2/022; A61F 2/0077; A61F 2002/0081; A61F 2210/0095;
(Continued)

(56) References Cited

U.S. PATENT DOCUMENTS 4,720,384 A * 1/1988 Di Luccio ............ A61K 9/0092
264/561
5,262,055 A * 11/1993 Bae .......................... A61F 2/022
210/321.75

(Continued)

FOREIGN PATENT DOCUMENTS

WO 2016/014987 1/2016

OTHER PUBLICATIONS

International Search Report and Written Opinion issued for Application No. PCT/US2018/049675, dated Nov. 19, 2018, 10 pages.
(Continued)

*Primary Examiner* — Paul B Prebilic
(74) *Attorney, Agent, or Firm* — Meunier Carlin & Curfman LLC

(57) ABSTRACT

Porous implantable devices for housing one or more therapeutic agents are disclosed herein. The implantable devices
(Continued)

include a porous outer wall defining an interia or void. The interior void houses a carrier material carrying a first therapeutic agent. The implantable devices are made by patterning at least a portion of a polymerizable substrate into a polymerized three-dimensional porous outer wall surrounding an interior void. This can be achieved by two-photon polymerization techniques. A first therapeutic agent is then added to the interior void, which is then sealed. Methods of treating diseases using the implantable devices are disclosed herein. The methods include implanting the implantable device at a target area and locally releasing a therapeutically effective dosage of a first therapeutic agent from the interior void. The implantable devices can also be used in methods of screening potentially therapeutic agents for desired biological responses.

14 Claims, 15 Drawing Sheets

(51) Int. Cl.
  A61K 38/17    (2006.01)
  A61F 2/00     (2006.01)
  A61K 35/30    (2015.01)
  A61L 31/14    (2006.01)
(52) U.S. Cl.
  CPC ........ *A61K 38/1767* (2013.01); *A61L 31/048* (2013.01); *A61L 31/146* (2013.01); *A61F 2002/0081* (2013.01); *A61F 2210/0095* (2013.01); *A61F 2230/0069* (2013.01); *A61F 2250/0067* (2013.01)
(58) Field of Classification Search
  CPC ..... A61F 2230/0069; A61F 2250/0067; A61K 35/30; A61K 38/1767; A61L 31/146; A61L 31/048
  See application file for complete search history.

(56) References Cited

U.S. PATENT DOCUMENTS

| | | | |
|---|---|---|---|
| 5,665,065 A | 9/1997 | Colman et al. | |
| 7,291,497 B2 | 11/2007 | Holmf et al. | |
| 8,815,276 B2 | 8/2014 | Nygaard et al. | |
| 2003/0064095 A1 | 4/2003 | Martin et al. | |
| 2003/0224033 A1* | 12/2003 | Li | A61K 9/0024 604/529 |
| 2005/0177118 A1 | 8/2005 | Hoganson et al. | |
| 2008/0051624 A1* | 2/2008 | Bonutti | A61F 2/4601 623/1.25 |
| 2008/0195196 A1 | 8/2008 | Asgari | |
| 2010/0255061 A1* | 10/2010 | de Juan, Jr. | A61P 27/02 604/93.01 |
| 2012/0078362 A1* | 3/2012 | Haffner | A61F 9/00781 623/6.13 |
| 2013/0304031 A1* | 11/2013 | Varner | A61F 9/0017 604/521 |

OTHER PUBLICATIONS

International Preliminary Report on Patentability Opinion issued for Application No. PCT/US2018/049675, dated Mar. 19, 2020, 8 pages.
Ahmed, E. M. Hydrogel: Preparation, characterization, and applications: A review. Journal of advanced research 6, 105-121, doi:10.1016/j.jare.2013.07.006 (2015).
Alam, M. I. et al. Strategy for effective brain drug delivery. European journal of pharmaceutical sciences : official journal of the European Federation for Pharmaceutical Sciences 40, 385-403, doi:10.1016/j.ejps.2010.05.003 (2010).
Allen, T. M. & Cullis, P. R. Drug delivery systems: entering the mainstream. Science 303, 1818-1822, doi:10.1126/science.1095833 (2004).
Barry, B. W. Novel mechanisms and devices to enable successful transdermal drug delivery. European journal of pharmaceutical sciences : official journal of the European Federation for Pharmaceutical Sciences 14, 101-114 (2001).
Baumann, M. D. et al. An injectable drug delivery platform for sustained combination therapy. Journal of controlled release : official journal of the Controlled Release Society 138, 205-213, doi:10.1016/j.jconrel.2009.05.009 (2009).
Biondi, M., Ungaro, F., Quaglia, F. & Netti, P. A. Controlled drug delivery in tissue engineering. Advanced drug delivery reviews 60, 229-242, doi:10.1016/j.addr.2007.08.038 (2008).
Bracaglia, L. G. et al. 3D printing for the design and fabrication of polymer-based gradient scaffolds. Acta biomaterialia, doi:10.1016/j.actbio.2017.03.030 (2017).
Cohen-Pfeffer, J. L. et al. Intracerebroventricular Delivery as a Safe, Long-Term Route of Drug Administration. Pediatric neurology 67, 23-35, doi:10.1016/j.pediatmeurol.2016.10.022 (2017).
Crepeau, A. Z. & Sirven, J. I. Management of Adult Onset Seizures. Mayo Clinic proceedings 92, 306-318, doi:10.1016/j.mayocp.2016.11.013 (2017).
Davies, N. M. Biopharmaceutical considerations in topical ocular drug delivery. Clinical and experimental pharmacology & physiology 27, 558-562 (2000).
De Jong, W. H. & Borm, P. J. Drug delivery and nanoparticles:applications and hazards. International journal of nanomedicine 3, 133-149 (2008).
Ennezat, P. V. et al. From evidence-based medicine to personalized medicine, with particular emphasis on drug-safety monitoring. Archives of cardiovascular diseases, 413-419, (2017). doi:10.1016/j.acvd.2017.01.011 (2017).
Eriksdotter-Jonhagen, M. et al. Encapsulated cell biodelivery of nerve growth factor to the Basal forebrain in patients with Alzheimer's disease. Dementia and geriatric cognitive disorders 33, 18-28, doi:10.1159/000336051 (2012).
Esquenazi, Y. et al. Surgical Resection for Epilepsy Following Cerebral Gunshot Wounds. World neurosurgery 95, 276-284, doi:10.1016/j.wneu.2016.08.041 (2016).
Eyjolfsdottir, H. et al. Targeted delivery of nerve growth factor to the cholinergic basal forebrain of Alzheimer's disease patients: application of a second-generation encapsulated cell biodelivery device. Alzheimer's research & therapy 8, 30, doi:10.1186/s13195-016-0195-9 (2016).
Ferreira, D. et al. Brain changes in Alzheimer's disease patients with implanted encapsulated cells releasing nerve growth factor. Journal of Alzheimer's disease : JAD 43, 1059-1072, doi:10.3233/JAD-141068 (2015).
Gaudana, R., Ananthula, H. K., Parenky, A. & Mitra, A. K. Ocular drug delivery. The AAPS journal 12, 348-360, doi:10.1208/s12248-010-9183-3 (2010).
GmbH, N. Nanoscribe Photonic Professional GT Data Sheet, <https://www.nanoscribe.de/files/4514/8179/1302/DataSheet_PPGT_V04_2016_web.pdf> (2016).
Groll, J. et al. Biofabrication: reappraising the definition of an evolving field. Biofabrication 8, 013001, doi:10.1088/1758-5090/8/1/013001 (2016).
Groothuis, D. R. The blood-brain and blood-tumor barriers: a review of strategies for increasing drug delivery. Neuro-oncology 2, 45-59 (2000).
Guillaume, D. J., Huhn, S. L., Selden, N. R. & Steiner, R. D. Cellular therapy for childhood neurodegenerative disease. Part I: rationale and preclinical studies. Neurosurgical focus 24, E22, doi:10.3171/FOC/2008/24/3-4/E21 (2008).
Haney, M. J. et al. Exosomes as drug delivery vehicles for Parkinson's disease therapy. Journal of controlled release : official journal of the Controlled Release Society 207, 18-30, doi:10.1016/j.jconrel.2015.03.033 (2015).
Hoffman, A. S. Hydrogels for biomedical applications. Advanced drug delivery reviews 54, 3-12 (2002).

(56) References Cited

OTHER PUBLICATIONS

Hong, N., Yang, G. H., Lee, J. & Kim, G. 3D bioprinting and its in vivo applications. Journal of biomedical materials research. Part B, Applied biomaterials, doi:10.1002/jbm.b.33826 (2017).

Huynh, G. H., Deen, D. F. & Szoka, F. C., Jr. Barriers to carrier mediated drug and gene delivery to brain tumors. Journal of controlled release : official journal of the Controlled Release Society 110, 236-259, doi:10.1016/j.jconrel.2005.09.053 (2006).

Jernigan, T. L., Baare, W. F., Stiles, J. & Madsen, K. S. Postnatal brain development: structural imaging of dynamic neurodevelopmental processes. Progress in brain research 189, 77-92, doi:10.1016/B978-0-444-53884-0.00019-1 (2011).

Jonas, O. et al. An implantable microdevice to perform high-throughput in vivo drug sensitivity testing in tumors. Science translational medicine 7, 284ra257, doi:10.1126/scitranslmed.3010564 (2015).

Jonathan, G. & Karim, A. 3D printing in pharmaceutics: A new tool for designing customized drug delivery systems. International journal of pharmaceutics 499, 376-394, doi:10.1016/j.ijpharm.2015.12.071 (2016).

Jones, E. G. & Rakic, P. Radial columns in cortical architecture: it is the composition that counts. Cereb Cortex 20, 2261-2264, doi:10.1093/cercor/bhq127 (2010).

Kanellakopoulou, K. & Giamarellos-Bourboulis, E. J. Carrier systems for the local delivery of antibiotics in bone infections. Drugs 59, 1223-1232 (2000).

Karami, A. et al. Changes in CSF cholinergic biomarkers in response to cell therapy with NGF in patients with Alzheimer's disease. Alzheimer's & dementia : the journal of the Alzheimer's Association 11, 1316-1328, doi:10.1016/j.jalz.2014.11.008 (2015).

Kasper, F. K., Tanahashi, K., Fisher, J. P. & Mikos, A. G. Synthesis of poly(propylene fumarate). Nature protocols 4, 518-525, doi:10.1038/nprot.2009.24 (2009).

Killoy, W. J. Chemical treatment of periodontitis: local delivery of antimicrobials. International dental journal 48, 305-315 (1998).

Klinghoffer, R. A. et al. A technology platform to assess multiple cancer agents simultaneously within a patient's tumor. Science translational medicine 7, 284ra258, doi:10.1126/scitranslmed.aaa7489 (2015).

Kordower, J. H. et al. Clinicopathological findings following intraventricular glial-derived neurotrophic factor treatment in a patient with Parkinson's disease. Annals of neurology 46, 419-424 (1999).

Kuo, C., Wilson, E., Fuson, A., Gandhi, N., Monfaredi, R., Jenkins, A., Romera, M., Santoro, M., Fisher, J. P., Cleary, K., Reilly, B. Repair of Tympanic Membrane Perforations with Customized, Bioprinted Ear Grafts Using Chinchilla Models. Tissue Engineering Part A, doi: 10.1089/ten.TEA.2017.0246 (2017).

Langer, R. Drug delivery and targeting. Nature 392, 5-10 (1998).

Lockman, P. R. et al. In vivo and in vitro assessment of baseline blood-brain barrier parameters in the presence of novel nanoparticles. Pharmaceutical research 20, 705-713 (2003).

Lockman, P. R., Mumper, R. J., Khan, M. A. & Allen, D. D. Nanoparticle technology for drug delivery across the blood-brain barrier. Drug development and industrial pharmacy 28, 1-13, doi:10.1081/DDC-120001481 (2002).

Mathias, N. R. & Hussain, M. A. Non-invasive systemic drug delivery: developability considerations for alternate routes of administration. Journal of pharmaceutical sciences 99, 1-20, doi:10.1002/jps.21793 (2010).

McGovern, R. A., Banks, G. P. & McKhann, G. M., 2nd. New Techniques and Progress in Epilepsy Surgery. Current neurology and neuroscience reports 16, 65, doi:10.1007/s11910-016-0661-6 (2016).

Mirnezami, R., Nicholson, J. & Darzi, A. Preparing for precision medicine. The New England journal of medicine 366, 489-491, doi:10.1056/NEJMp1114866 (2012).

Mironov, V., Boland, T., Trusk, T., Forgacs, G. & Markwald, R. R. Organ printing: computer-aided jet-based 3D tissue engineering. Trends in biotechnology 21, 157-161, doi:10.1016/S0167-7799(03)00033-7 (2003).

Misra, A., Ganesh, S., Shahiwala, A. & Shah, S. P. Drug delivery to the central nervous system: a review. Journal of pharmacy & pharmaceutical sciences : a publication of the Canadian Society for Pharmaceutical Sciences, Societe canadienne des sciences pharmaceutiques 6, 252-273 (2003).

Neuwelt, E. A. et al. Engaging neuroscience to advance translational research in brain barrier biology. Nature reviews. Neuroscience 12, 169-182, doi:10.103 8/nrn2995 (2011).

Nguyen, K. T., West, J. L. Photopolymerizable hydrogels for tissue engineering applications. Biomaterials. 23, 4307-4317, doi: 10.1016/S0142-9612(02)00175-8 (2002).

Pardridge, W. M. CSF, blood-brain barrier, and brain drug delivery. Expert opinion on drug delivery 13, 963-975, doi:10.1517/17425247.2016.1171315 (2016).

Pardridge, W. M. The blood-brain barrier: bottleneck in brain drug development. NeuroRx : the journal of the American Society for Experimental NeuroTherapeutics 2, 3-14, doi:10.1602/neurorx.2.1.3 (2005).

Placone, J. K., Navarro, J., Laslo, G. W., Lerman, M. J., Gabard, A. R., Herendeen, G. J., Falco, E. E., Tomblyn, S., Burnett, L, Fisher, J. P. Development and Characterization of a 3D Printed, Keratin-Based Hydrogel. Annals of Biomedical Engineering 45, 237-248, doi: 10.1007/s10439-016-1621-7 (2017).

Richards Grayson, A. C. et al. Multi-pulse drug delivery from a resorbable polymeric microchip device. Nature materials 2, 767-772 (2003).

Rossi, F. & Cattaneo, E. Opinion: neural stem cell therapy for neurological diseases: dreams and reality. Nature reviews. Neuroscience 3, 401-409, doi:10.1038/nrn809 (2002).

Rossi, F. et al. Characterization and degradation behavior of agar-carbomer based hydrogels for drug delivery applications: solute effect. International journal of molecular sciences 12, 3394-3408, doi:10.3390/ijms12063394 (2011).

Rossi, F. et al. Sustained Delivery of Chondroitinase ABC from Hydrogel System. Journal of functional biomaterials 3, 199-208, doi:10.3390/jfb3010199 (2012).

Selden, N. R. et al. Central nervous system stem cell transplantation for children with neuronal ceroid lipofuscinosis. Journal of neurosurgery. Pediatrics 11, 643-652, doi:10.3171/2013.3.PEDS12397 (2013).

Selden, N. R., Guillaume, D. J., Steiner, R. D. & Huhn, S. L. Cellular therapy for childhood neurodegenerative disease. Part II: clinical trial design and implementation. Neurosurgical focus 24, E23, doi:10.3171/FOC/2008/24/3-4/E22 (2008).

Short, B. G. Safety evaluation of ocular drug delivery formulations: techniques and practical considerations. Toxicologic pathology 36, 49-62, doi:10.1177/0192623307310955 (2008).

Stiles, J. & Jernigan, T. L. The basics of brain development. Neuropsychology review 20, 327-348, doi:10.1007/s11065-010-9148-4 (2010).

Sun, T. & Hevner, R. F. Growth and folding of the mammalian cerebral cortex: from molecules to malformations. Nature reviews. Neuroscience 15, 217-232, doi:10.1038/nrn3707 (2014).

Torii, M., Hashimoto-Torii, K., Levitt, P. & Rakic, P. Integration of neuronal clones in the radial cortical columns by EphA and ephrin-A signalling. Nature 461, 524-528, doi:10.1038/nature08362 (2009).

Vasefi, F., MacKinnon, N., Farkas, D. L. & Kateb, B. Review of the potential of optical technologies for cancer diagnosis in neurosurgery: a step toward intraoperative neurophotonics. Neurophotonics 4, 011010, doi:10.1117/1.NPh.4.1.011010 (2017).

Ventola, C. L. Medical Applications for 3D Printing: Current and Projected Uses. P & T : a peer-reviewed journal for formulary management 39, 704-711 (2014).

Wahlberg, L. U. et al. Targeted delivery of nerve growth factor via encapsulated cell biodelivery in Alzheimer disease: a technology platform for restorative neurosurgery. Journal of neurosurgery 117, 340-347, doi:10.3171/2012.2.JNS11714 (2012).

Wicki, A., Witzigmann, D., Balasubramanian, V. & Huwyler, J. Nanomedicine in cancer therapy: challenges, opportunities, and

(56) References Cited

OTHER PUBLICATIONS clinical applications. Journal of controlled release: official journal of the Controlled Release Society 200, 138-157, doi:10.1016/j.jconrel. 2014.12.030 (2015).

Yi, H. G. et al. A 3D-printed local drug delivery patch for pancreatic cancer growth suppression. Journal of controlled release : official journal of the Controlled Release Society 238, 231-241, doi:10. 1016/j.jconrel.2016.06.015 (2016).

Yi, X., Manickam, D. S., Brynskikh, A. & Kabanov, A. V. Agile delivery of protein therapeutics to CNS. Journal of controlled release : official journal of the Controlled Release Society 190, 637-663, doi:10.1016/j.jconrel.2014.06.017 (2014).

Yoganandan, N. & Pintar, F. A. Biomechanics of temporo-parietal skull fracture. Clin Biomech (Bristol, Avon) 19, 225-239, doi:10. 1016/j.clinbiomech.2003.12.014 (2004).

Zema, L., Melocchi, A., Maroni, A. & Gazzaniga, A. Three-Dimensional Printing of Medicinal Products and the Challenge of Personalized Therapy. Journal of pharmaceutical sciences 106, 1697-1705, doi:10.1016/j.xphs.2017.03.021 (2017).

Kompella, U. B. & Lee, V. H. Delivery systems for penetration enhancement of peptide and protein drugs: design considerations. Advanced drug delivery reviews 46, 211-245 (2001).

Timpka, J., Nitu, B., Datieva, V., Odin, P. & Antonini, A. Device-Aided Treatment Strategies in Advanced Parkinson's Disease. International review of neurobiology 132, 453-474, doi:10.1016/bs.irn. 2017.03.001 (2017).

Gewirtz, D. A., Bristol, M. L. & Yalowich, J. C. Toxicity issues in cancer drug development. Curr Opin Investig Drugs 11, 612-614 (2010).

\* cited by examiner

POROUS IMPLANTABLE DEVICES

CROSS REFERENCE TO RELATED APPLICATIONS

This application claims the benefit of U.S. Provisional Application No. 62/554,680, filed Sep. 6, 2017, which is incorporated by reference in its entirety for all purposes.

TECHNICAL FIELD

This invention relates to the delivery of therapeutic agents, and more particularly to localized delivery via implantable devices.

BACKGROUND

A significant challenge in modern medicine is the manufacturing of therapies that maximize the precision and personalization for individual patients. The needs for such technologies in medicine are wide-ranging; many, if not most, medical conditions involve the dysfunction of specific organs or the occurrence of diseased regions within otherwise healthy tissues. These include but are not restricted to needs in direct applications for cancer therapy; interventions in ocular disorders; and treatment of neurological disorders such as Parkinson's disease, Alzheimer's disease, and epilepsy, among others. Despite the focal nature of these disease processes, current therapies are delivered systemically, exposing the rest of the body to unwanted side effects and minimizing potential efficacy. As such, designing a versatile therapeutic delivery platform that can be precisely tailored for each patient is paramount.

The delivery of therapeutic agents into their respective targets presents several challenges. Systemic pharmacological delivery has particular limitations given the need for targeting of specific desired regions without affecting surrounding unaffected areas and tissues, as well as obstructions by various blood-tissue barriers which may restrict delivery. The more straightforward solution has been through the use of implantable devices and gels which are applied directly into afflicted regions. Such interventions maximize concentrations of local drug delivery while minimizing toxicity and side-effects experienced by systemic delivery options. Yet, current devices have several shortcomings in regards to implementations in complex systems such as the central nervous and ocular systems, as they are typically obtrusive and invasive in size, lacking in the fine control necessary for precise delivery, are not customizable for individual patients, and often have added complexities in releasing therapeutic materials. Therefore, a need persists for devices that can provide pinpoint precision of therapeutic delivery, maximize efficacy, reduce side-effects and damage, and account for specific individual patient needs.

SUMMARY

The implantable devices disclosed herein are configured to house therapeutic agents for the treatment of diseases or disorders, for example, via localized delivery of those therapeutic agents to a target area within an organ or tissue. The implantable devices are small enough to be delivered unobtrusively, for example, through a very small incision or via a needle. The precise placement of the implantable device enables highly localized delivery of therapeutic agents to the target area. The highly localized delivery diminishes the occurrence of side effects during the treatment of a disease or disorder. The fabrication method of the implantable device enables precise design of micron sized features, as well as the customization of design parameters which can, for example, be tailored to meet the needs of an individual patient.

The implantable devices include a porous outer wall defining an interior void, a carrier material and a first therapeutic agent housed inside the interior void. The total volume of the implantable device can range from about 40 nanoliters to about 10 microliters. The implantable devices are made by patterning at least a portion of a polymerizable substrate into a polymerized three-dimensional porous outer wall, for example, using two photon polymerization techniques. Unpolymerized substrate is then removed to create an interior void surrounded by the porous outer wall. A first therapeutic agent is added to the interior void, which is then sealed to create the implantable device. Methods of treating diseases or disorders using the implantable devices are also disclosed herein. The methods include implanting the implantable device into a target area and locally releasing a therapeutically effective dosage of a first therapeutic agent over time from an interior void of the implantable device. The implantable devices can also be used in methods of screening potentially therapeutic agents for a desired biological response, for example, by implanting one or more implantable devices into a test tissue, locally releasing the potentially therapeutic agent(s), and monitoring a response from the test tissue, wherein the response is indicative of the therapeutic effectiveness of the potentially therapeutic agent.

The details of one or more embodiments of the invention are set forth in the accompanying drawings and the description below. Other features, objects, and advantages of the invention will be apparent from the description and drawings, and from the claims.

DESCRIPTION OF DRAWINGS

In FIGS. 14E-14G, the autofluoresence of the implantable device has been subtracted. (h-l) hiNPCs underwent a differentiation protocol within an implantable device and were then fixed and stained for GFP (h) and neuronal maturation marker MAP2 (i). The merged image (j) shows GFP positive hiNPCs that are also MAP2 positive. Side (k) and oblique (l) views demonstrate that mature neuronal cells are localized throughout the implantable device.

DETAILED DESCRIPTION

Figure 1:
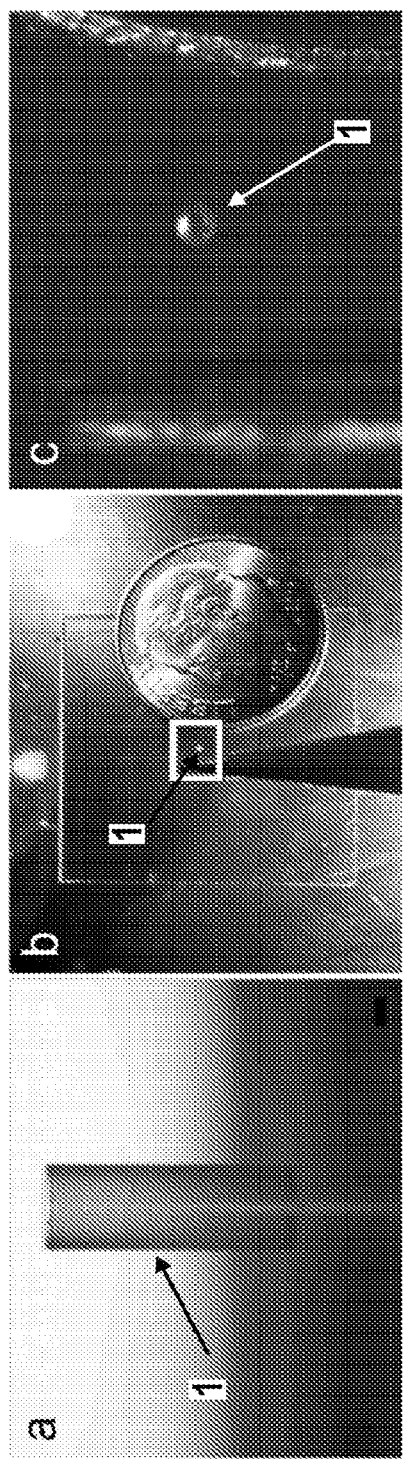
FIGS. 1A-1G show the implantable device and its relative size. (a) Light microscopy image of the implantable device showing its relative proportions and porous exterior. Scale bar=100 µm. (b and c) relative size of the implantable device. Implantable device from the top-down viewpoint is displayed in relation to a pencil tip (to the left) and dime (to the right) to reflect its miniature size. (c) is a higher magnification of the boxed area in (b). (d) Schematic of the workflow for ex vivo implantation of the implantable device. Implantable devices are first filled with the desired therapeutic molecules. (e) Implantable devices are then capped. (f) The device is then inserted into the targeted tissue of interest (in this example, a mouse cortex). (g) The contents are allowed to elute into the local surrounding areas of the tissue.
Figure 1:
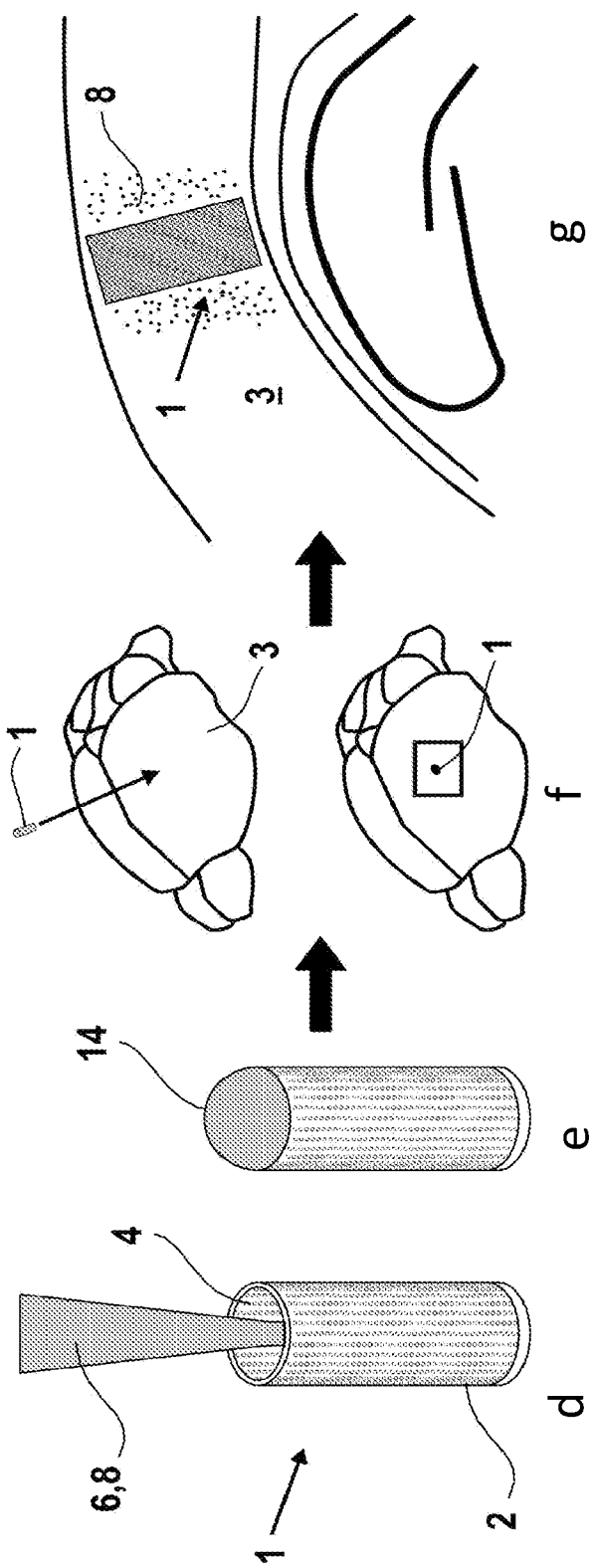

One technology with the potential to improve precision and personalization for individual patients is 3D printing and fabrication, whereby delivery methods may be custom-designed with a wide range of materials. To date, several applications have utilized 3D printing technologies for biological contexts, particularly in the fabrications of tissues. More recent approaches have begun to explore the incorporation of therapeutic molecules into biodegradable patches that can be applied to the area of interest. However, the integration of pharmacological agents or cells within these materials is a challenge, as the printing process may affect cell viability or drug stability and elution.

Given these current shortcomings, there exists a need for a customizable device that offers both a precise means of delivery along with a flexibility of design. Disclosed herein is a needle-sized porous implantable device: a micron-scale perforated container printed with nanometer-level resolution and filled with therapeutic agents for precise delivery directly to the tissue of interest. The device can be printed using two photon polymerization techniques. The use of two photon polymerization printing allows for the fabrication of porous implantable devices that are structurally sound enough to withstand the implantation process and small enough to be directly and unobtrusively implanted, for example, in delicate tissues such as the brain.

Definitions

Terms used throughout this application are to be construed with ordinary and typical meaning to those of ordinary skill in the art. However, Applicant desires that the following terms be given the particular definition as defined below.

As used in the specification and claims, the singular form "a," "an," and "the" include plural references unless the context clearly dictates otherwise. For example, the term "a cell" includes a plurality of cells, including mixtures thereof.

The terms "about" and "approximately" are defined as being "close to" as understood by one of ordinary skill in the art. In one non-limiting embodiment the terms are defined to be within 10%. In another non-limiting embodiment, the terms are defined to be within 5%. In still another non-limiting embodiment, the terms are defined to be within 1%.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

As used herein, the term "therapeutic agent" refers to an agent that will elicit the biological or medical response of a tissue, system, animal, or human that is being sought by the researcher, veterinarian, medical doctor or other clinician over a generalized period of time. For example, in some embodiments, a desired response is the amelioration of a disease or a disorder. A "therapeutically effective" amount is the amount of the agent that will elicit the desired biological or medical response. A "neuromodulatory agent" is a therapeutic agent having the ability to diffuse through large areas of the nervous system so as to regulate a diverse population of neurons.

The term "carrier material" means a compound, composition, substance, or structure that, when in combination with a therapeutic agent, aids or facilitates preparation, storage, administration, delivery, effectiveness, selectivity, or any other feature of the therapeutic agent for its intended use or purpose. For example, a carrier material can be selected to minimize any degradation of the therapeutic agent and to minimize any adverse side effects in the subject.

"Biocompatible" generally refers to a material and any metabolites or degradation products thereof that are generally non-toxic to the recipient and do not cause any significant adverse effects to the subject.

"Biodegradable" generally refers to a material that will degrade or erode under physiologic conditions to smaller units or chemical species that are capable of being metabolized, eliminated, or excreted by the subject. The degradation time is a function of polymer composition and morphology. Suitable degradation times are from days to months.

The term "polypeptide" is used in its broadest sense to refer to a compound of two or more subunit amino acids, amino acid analogs, or peptidomimetics. The subunits may be linked by peptide bonds. In another embodiment, the subunit may be linked by other bonds, e.g. ester, ether, etc.

As used herein the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is commonly called a polypeptide or a protein.

The terms "polynucleotide" and "oligonucleotide" are used interchangeably, and refer to a polymeric form of nucleotides of any length, either deoxyribonucleotides or ribonucleotides, or analogs thereof. Polynucleotides may have any three-dimensional structure, and may perform any function, known or unknown. Polynucleotide can refer to a sequence of genomic, synthetic, or recombinant origin and may be double-stranded or single-stranded, whether representing the sense or anti-sense strand. The following are non-limiting examples of polynucleotides: a gene or gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, genomic DNA, synthetic DNA, nucleic acid probes, and primers. The polynucleotide may contain chemical modifications. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine (T) when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

The term "small molecule" refers to a molecule, such as an organic or organometallic compound, with a molecular weight of less than 2,000 Daltons, more preferably less than 1,500 Daltons, most preferably less than 1,000 Daltons. The small molecule can be a hydrophilic, hydrophobic, or amphiphilic compound.

As used herein, the term "cell-derived material" can refer to any material released from a cell into the surrounding environment. Cell-derived materials can be, for example, paracrine, endocrine, autocrine, juxtracrine, or synaptic signals. Cell-derived materials can also be, for example, extracellular vesicles, which can include vesicles released from cells by any mechanism. "Extracellular vesicles" includes exosomes which are released from multivesicular bodies and microvesicles that are shed from the cell surface. "Extracellular vesicles" includes vesicles created by exocytosis or ectocytosis. "Extracellular vesicles" encompasses exosomes released from multivesicular bodies, vesicles released by reverse budding, fission of membrane(s), multivesicular endosomes, ectosomes, microvesicles, microparticles, and vesicles released by apoptotic bodies, and hybrid vesicles containing plasma membrane components. Extracellular vesicles can contain proteins, nucleic acids, lipids, and other molecules common to the originating cell.

The terms "treat," "treating," "treatment," and grammatical variations thereof as used herein, include partially or completely delaying, alleviating, mitigating or reducing the intensity of one or more attendant symptoms of a disease, disorder or condition and/or alleviating, mitigating or impeding one or more causes of a disorder or condition. Treatments according to the invention may be applied preventively, prophylactically, palliatively or remedially. Prophylactic treatments are administered to a subject prior to onset (e.g., before obvious signs of cancer), during early onset (e.g., upon initial signs and symptoms of cancer), or after an established development of cancer. Prophylactic administration can occur for several days to years prior to the manifestation of symptoms of an infection.

The terms "patient", or "subject" are defined herein to include animals such as mammals, including, but not limited to, primates (e.g., humans), cows, sheep, goats, horses, dogs, cats, rabbits, rats, mice and the like. In some embodiments, the patient or subject is a human.

DESCRIPTION

The implantable devices disclosed herein are configured to house therapeutic agents for the treatment of diseases or disorders, for example, via localized delivery of those therapeutic agents to a target area of an organ or tissue. The implantable devices are small enough to be delivered unobtrusively, for example, through a very small incision or via a needle. As shown in FIG. 1D, the interior void 4 of implantable device 1 is filled with a mixture of carrier material 6 and therapeutic agent 8, then sealed with end structure 14. The precise placement of the implantable device 1 enables highly localized delivery of therapeutic agents 8 to the target area 3 (the brain in FIG. 1D). The highly localized delivery diminishes the occurrence of side effects during the treatment of a disease or disorder. The fabrication method of the implantable device enables precise design of micron sized features, as well as the customization of design parameters which can, for example, be tailored to meet the needs of an individual patient.

An example embodiment of an implantable device is shown in FIGS. 2A-2D. The implantable device 1 includes a porous outer wall 2 that surrounds and defines the interior void 4. The implantable device 1 is small to minimize invasiveness while still enabling the addition of the carrier material 6 and therapeutic agent 8 into the interior void 4. The total volume of the implantable device 1 can be from about 40 nanoliters to about 10 microliters. In some embodiments, the volume is from about 40 nanoliters to about 500 nanoliters, including, for example, about 40 nanoliters, about 60 nanoliters, about 80 nanoliters, about 100 nanoliters, about 120 nanoliters, about 140 nanoliters, about 160 nanoliters, about 180 nanoliters, about 200 nanoliters, about 220 nanoliters, about 240 nanoliters, about 260 nanoliters, about 280 nanoliters, about 300 nanoliters, about 320 nanoliters, about 340 nanoliters, about 360 nanoliters, about 380 nanoliters, about 400 nanoliters, about 420 nanoliters, about 440 nanoliters, about 460 nanoliters, about 480 nanoliters or about 500 nanoliters.

In some embodiments, the porous outer wall 2 is cylindrical in shape. A cylindrical shape can be advantageous, for example, to facilitate delivery through a syringe or a needle, and to mimic tissue structures (for example, cortical columns of the brain). However, the shape and thickness of the porous outer wall can be adapted to suit different needs, tissue structures, and/or to vary the release kinetics of the therapeutic agent 8. For example, the porous outer wall could alternatively be spherical, cubic, a prism, a pyramid, a frustocone, hourglass, or any shape with curved sides. A cross section of the porous outer wall 2 could take the shape of circular, triangular, square, polygonal having 4, 5, 6, 7, 8, 9, 10 or more sides.

Referring now to FIG. 2C, the thickness 12 of the porous outer wall 2 provides the structural integrity of the implantable device 1. The thickness 12 of the porous outer wall 2 and its overall ratio to the inner diameter 10 can be tailored to alter release rate, degradation time, structural integrity, and the overall volume of the implantable device 1 for delivery to the target area 3. The thickness of the porous outer wall can be, in some embodiments, from about 20 to about 10,000 microns. In some embodiments, the thickness of the porous outer wall can be from about 20 to about 1000 microns, or from about 20 to about 500 microns, including about 40 microns, about 60 microns, about 80 microns, about 100 microns, about 120 microns, about 140 microns, about 160 microns, about 180 microns, about 200 microns, about 220 microns, about 240 microns, about 260 microns, about 280 microns, and about 300 microns about 320 microns, about 340 microns, about 360 microns, about 380 microns, about 400 microns, about 420 microns, about 460 microns, about 480 microns, and about 500 microns.

In some embodiments, the inner diameter 10 of the interior void 4 is from about 10 to about 20 times greater than the thickness 12 of the porous outer wall 2, including, for example, about 10 times greater, about 11 times greater, about 12 times greater, about 13 times greater, about 14 times greater, about 15 times greater, about 16 times greater, about 17 times greater, about 18 times greater, about 19 times greater, and about 20 times greater.

The interior void 4 of the implantable device is sealed by at least one end structure 14, as shown in FIG. 1D. The end structure 14 can be formed of a different material than the porous outer wall. In some embodiments, end structure 14 can be formed of a biocompatible sealant. Alternatively, the end structure 14 can be formed of the same material as the porous outer wall.

Porous outer wall 2 includes pore openings 16, as shown in FIG. 2D. The pore openings have widths ranging from about 0.01 micrometers to about 25 micrometers, including, for example, about 0.01 micrometers, about 0.02 micrometers, about 0.03 micrometers, about 0.04 micrometers, about 0.05 micrometers, about 0.1 micrometers, about 0.15 micrometers, about 0.2 micrometers, about 0.25 micrometers, about 0.3 micrometers, about 0.35 micrometers, about 0.4 micrometers, about 0.45 micrometers, about 0.5 micrometers, about 1.0 micrometers, about 1.5 micrometers, about 2.0 micrometers, about 2.5 micrometers, about 3.0 micrometers, about 3.5 micrometers, about 4.0 micrometers, about 4.5 micrometers, about 5.0 micrometers, about 5.5 micrometers, about 6.0 micrometers, about 6.5 micrometers, about 7.0 micrometers, about 7.5 micrometers, about 8.0 micrometers, about 8.5 micrometers, about 9.0 micrometers, about 9.5 micrometers, about 10.0 micrometers, about 10.5 micrometers, about 11.0 micrometers, about 11.5 micrometers, about 12.0 micrometers, about 12.5 micrometers, about 13.0 micrometers, about 13.5 micrometers, about 14.0 micrometers, about 14.5 micrometers, about 15.0 micrometers, about 15.5 micrometers, about 16 micrometers, about 16.5 micrometers, about 17 micrometers, about 17.5 micrometers, about 18 micrometers, about 18.5 micrometers, about 19 micrometers, about 19.5 micrometers, about 20 micrometers, about 20.5 micrometers, about 21 micrometers, about 21.5 micrometers, about 22 micrometers, about 22.5 micrometers, about 23 micrometers, about 23.5 micrometers, about 24 micrometers, about 24.5 micrometers, and about 25 micrometers. In some embodiments, the pore openings 16 have widths that are large enough to enable elution of the therapeutic agent 8, but small enough to prevent nearby cells from infiltrating the interior void 4. For example, the pore openings 16 can be from about 3 micrometers to about 7 micrometers in width to prevent cell movement through the wall. In the example shown in FIG. 2D, the width of pore openings 16 is about 5 micrometers.

The density of pore openings 16 can be tailored to adjust the release kinetics of therapeutic agent 8. In some embodiments, the porous outer wall 2 has a pore density of from about 200 to about 50,000 pores per millimeter squared. In some embodiments, the porous outer wall 2 has a pore density of from about 200 to 25,000 pores per millimeter squared, including about 200, about 500, about 1,000, about 1,500, about 2,000, about 2,500, about 3,000, about 3,500, about 4,000, about 4,500, about 5,000, about 5,500, about 6,000, about 6,500, about 7,000, about 7,500, about 8,000, about 8,500, about 9,000, about 9,500, about 10,000, about 10,500, about 11,000, about 11,500, about 12,000, about 12,500, about 13,000, about 13,500, about 14,000, about 14,500, about 15,000, about 15,500, about 16,000, about 16,500, about 17,000, about 17,500, about 18,000, about 18,500, about 19,000, about 19,500, about 20,000, about 20,500, about 21,000, about 21,500, about 22,000, about 22,500, about 23,000, about 23,500, about 24,000, about 24,500, and about 25,000 pores per millimeter squared.

Other variables that can be tailored to alter release kinetics include the carrier material 6. In some embodiments, the carrier material 6 can be loaded with particles that contain the therapeutic material 8. These particles can, for example, release the therapeutic material upon the application of a stimulus. The stimulus could be, for example, ultrasound, near infrared light, or the presence of a particular activating compound in the environment surrounding the implantable device 1.

The porous outer wall 2 is formed of a biocompatible material. In some embodiments, the porous outer wall 2 is also formed of a biodegradable material, such as a biodegradable polymer. Degradability can be advantageous to prevent the risk of a longer term foreign body response. The degradability can also be advantageous, for example, to deliver one or more additional therapeutic agents that can be embedded within the porous outer wall 2. The degradation can take place via, for example, hydrolytic, oxidative, or enzymatic mechanisms, or by disintegration. The degradation rate is dependent at least on the molecular weight, the density of degradation sites, and the density of porogenic particles. These and other factors can be tailored to produce the desired degradation rate. In other embodiments, the biocompatible material is not degradable. General material properties can also be selected to optimize the implantable device for the desired application. For example, the rigidity of the material can be higher in an implantable device 1 intended to be implanted in a stiffer tissue.

FIGS. 12A-12E shows exemplary photographs of an implantable device 1 having a the porous outer wall 2 formed of biodegradable polymer poly(propylene fumarate) (PPF). In some embodiments, PPF can be cross-linked by 2PP in the presence of photoinitiator bis(2,4,6-trimethylbenzoyl) phenylphosphine oxide (BAPO) at a concentration of 1.5% wt/wt. Other photoinitiators and concentrations can be utilized for crosslinking PPF in other embodiments. Furthermore, other biodegradable and/or biocompatible polymers capable of being cross-linked could also be used to form the porous outer walls 2 of implantable device 1, including, but not limited to, gelatin methacrylate, keratin, and mono/diacrylate-modified polymers. The porous outer wall 2 can, in some embodiments, be detected by imaging modalities. For example, the porous outer wall 2 can be autofluorescent, or it can incorporate imaging agents to aid in its visualization. The imaging agents can be, for example, added fluorophores, radiopaque dyes or particles, or any contrast agent used to facilitate visualization using any biomedical imaging modality.

The porous outer wall 2 can also include additional therapeutic agents 8. These can be different from or the same as the therapeutic agents 8 housed in the interior void 4. Loading the porous outer wall 2, especially a porous outer wall 2 formed of a biodegradable material, with therapeutic agents 8 can extend the duration of treatment and/or allow for variation in delivery profile. For example, a therapeutic agent 8 housed in the interior void 4 can be eluted from carrier material 6 relatively quickly, during a first phase of treatment, whereas a therapeutic agent loaded into the porous outer wall 2 can be eluted relatively slowly while the biodegradable material degrades.

The interior void 4 of the implantable device 1 lends a versatility in the choice of therapeutic agent 8, facilitating custom design for particular disease states or patients. The interior void can filled with cells, drugs, and/or materials that are indicators of a biological change, such that the implantable device 1 can be used as a biosensor. For example, the carrier material 6 and/or the therapeutic agent 8 can give off a detectable electrical signal in the presence of a biological change, or the biological change may alter detectable fluorescent properties of the carrier material and/or the therapeutic agent.

Cell therapies can be limited by either the dispersal of cells from the target area, or by the attack of the donor cells by cells of the patient's immune system. The porous outer wall 2 can be used as a barrier that can increase the efficacy of cell therapy. When cells or cell-derived materials are used as therapeutic agents 8, the pore openings 16 of porous outer wall 2 can be sized to enable or disable the exit of the cells from the interior void 4, depending on the desired application. Any cell type capable of eliciting a therapeutic effect can be loaded into the implantable device and delivered to a patient.

In some embodiments, the interior void 4 can be filled with therapeutic agents 8 that are releasable via the pore openings 16 of the porous outer wall. For example, the therapeutic agent 8 can be a polynucleotide, a polypeptide, or a small molecule. In some embodiments, the therapeutic agent 8 can be a neuromodulatory agent. Neuromodulatory agents moderate brain development and function by altering neurobiological phenomena. Recent research indicates that localized delivery of neuromodulatory agents could improve treatment of a wide range of neurological disorders. Current systemic treatments saturate the broader neural network with neuromodulatory agents, failing to target specific nodes relative to the rest of the system. The implantable device 1 could solve this problem by enabling precise delivery of the neuromodulatory agents to specific nodes of the broader neural network. Exemplary neuromodulatory agents consist of neurotransmitters and their modulators, including but not limited to dopamine, serotonin, acetylcholine, histamine, glutamate, gamma-aminobutyric acid (GABA), norepinephrine, purines, nitric oxide, and endocannabinoids. In addition, pharmacological neuromodulatory agents may be utilized, including but not limited to anti-convulsants, anti-depressants, mood stabilizers, and cholinesterase inhibitors.

The therapeutic agent 8 can be housed in a carrier material 6. In addition to carrying the therapeutic agent 8, the carrier material 6 provides additional stability to the structure of the porous outer wall 2. Some potential alternatives for a carrier material 6 include, but are not limited to, agarose, biocytin, Matrigel, saline, gelatin, agar, and polyethylene glycol. Agarose, for example, can be used as carrier material at a concentration of, for example, from about 0.1% to about 0.5% by weight/volume, including about 0.1%, about 0.15%, about 0.2%, about 0.25%, about 0.3%, about 0.35%, about 0.4%, about 0.45%, and about 0.5%.

Implantable devices 1 are made by patterning at least a portion of a polymerizable substrate into polymerized three-dimensional porous outer wall 2. In some embodiments, the patterning is achieved by two-photon polymerization. Two-photon polymerization enables the printing of microscale or nanoscale structures with nanoscale resolution. It is based on the interaction of femtosecond laser radiation to induce highly localized chemical reactions, leading to the highly localized polymerization of photopolymerizable substrates. Photopolymerizable substrates that are transparent to infrared or near-infrared femtosecond lasers can be patterned anywhere within the volume of the substrate (not just at the surface). This enables the rapid tracing and polymerization of a precise structure (in this case, the three-dimensional porous outer wall 2) within an unpolymerized photopolymerizable substrate. In some embodiments, the walls are polymerized around the pores to create the porous outer walls 2. In other embodiments, a solid outer wall is polymerized and the pores are ablated into the polymerized wall to create porous outer wall 2. In some embodiments, the porous outer wall 2 can be patterned in under an hour.

After the porous outer walls 2 are patterned from the polymerizable substrate, unpolymerized substrate is removed, creating the interior void 4. In some embodiments, the removal step is performed by treating the substrate with propylene glycol monomethyl ether acetate (PGMEA) for about 30 minutes, after which the formed porous outer walls 2 are washed in 99% isopropyl alcohol and air-dried. In some embodiments, the removal step is performed by treating the substrate with isopropyl alcohol.

The implantable device may also be manufactured using other fabrication techniques, including optical lithography and micro electrical discharge machining (EDM). In one embodiment, the implantable device can be manufactured by micro machining a tube, and then using micro EDM to create the lattice of pores. The resolution of the micro EDM is about 10 micrometers. In an alternative embodiment, the pores are ablated using a laser. The resolution using a laser to ablate the pores is about 25 micrometers.

A therapeutic agent 8 is then added to the interior void 4. The addition of the therapeutic agent and sealing of the interior void can be performed, for example, using a stereotaxic apparatus and/or a microinjection device. In one embodiment, the therapeutic agent is added using a glass needle, particularly a Picospritzer®. The glass needle is attached to a stereotaxis apparatus at one end and the other end is inserted into the interior void 4, at which point the contents of the needle are released via the Picospritzer®. After the therapeutic agent 8 is added, the end of the interior void can be sealed with end structure 14 to create the implantable device 1. In alternative embodiments, the entire implantable device can be fabricated using a 3D printer. For example, the porous outer walls 2 can be 3D printed, the drugs or cell loaded into the interior void 4 via 3D printing, and the end cap 14 placed in a position to seal the interior void 4 via a 3D printer. In some embodiments, one or both of the end caps 14 can be porous.

Some embodiments of the fabrication method may also include steps of adding various agents to the polymerizable substrate prior to polymerization. For example, an imaging agent can be mixed into the polymerizable substrate to facilitate the ultimate visualization of the implantable device 1 using biomedical imaging modalities. Of course, an imaging agent could also be applied to the porous outer walls 2 after the fabrication of implantable device 1 without straying from the inventive concepts described herein. Additional therapeutic agents (beyond the one housed within the interior void 4) can be mixed into the polymerizable substrate for ultimate release from the porous outer walls 2 during degradation of the material.

The laser power used to fabricate the implantable structures can be, for example, from about 15 to about 40 mW. In some embodiments, the laser power can be from about 17 to about 38.5 mW, including about 17 mW, about 18 mW, about 19 mW, about 20 mW, about 21 mW, about 22 mW, about 23 mW, about 24 mW, about 25 mW, about 26 mW, about 27 mW, about 28 mW, about 29 mW, about 30 mW, about 31 mW, about 32 mW, about 33 mW, about 34 mW, about 35 mW, about 36 mW, about 36.5, about 37 mW, about 37.5 mW, about 38 mW and about 38.5 mW. The patterning or printing speed of the laser can be, for example, from 3,000 to 20,000 microns per second, including about 3,000 microns per second, about 4,000 microns per second, about 5,000 microns per second, about 6,000 microns per second, about 7,000 microns per second, about 8,000 microns per second, about 9,000 microns per second, about 10,000 microns per second, about 11,000 microns per second, about 12,000 microns per second, about 13,000 microns per second, about 14,000 microns per second, about 15,000 microns per second, about 16,000 microns per second, about 17,000 microns per second, about 18,000 microns per second, about 19,000 microns per second, and about 20,000 microns per second.

The method of fabrication and overall design of the implantable device 1 enables structural versatility (implantable device 1 can take any shape), material versatility (implantable device walls and carrier material can be varied and customized), and loading versatility (different therapeutic agents can be used). These advantages are particularly advantageous because they allow an implantable device 1 to be custom tailored to an individual patient or for a particular disease state. In some embodiments, the implantable device 1 can be custom built for a particular patient. The method of fabricating implantable device 1 for a particular patient can include gathering data from the individual patient prior to patterning the polymerizable substrate. Individual patient data can include, but is not limited to, images of the target area, anatomical measurements, a disease state or extent of progression, patient size, gender, age, family history, and/or genetic predispositions. The individual patient data can then be considered when determining design parameters of the implantable device 1. These design parameters can include, but are not limited to, selection of outer wall material and outer wall material characteristics such as (but not limited to) density, rigidity, degradation profile, and/or molecular weight, outer wall thickness and/or shape, pore density, pore opening width, properties that affect biocompatibility, content and density of porogens in the porous outer wall and/or in the carrier material, carrier material selection and carrier material properties such as (but not limited to) density, rigidity, degradation profile, and/or molecular weight, selection of therapeutic agents and therapeutic agent characteristics such as (but not limited to) dosage, cell density, and/or release rate.

The method of making the implantable devices 1 can include designing a model prior to patterning the porous outer wall 2. The model can include deviation and angular tolerances, which facilitate preservation of the resolution during fabrication. In some embodiments, the deviation tolerance is from about 0.4 microns to about 318 microns. In some embodiments, the angular tolerance is from about 0.5 degrees to about 30 degrees. The model can be used, for example, to simulate the therapeutic agent release profile. The design parameters of the implantable device 1 can be adjusted within the model to anticipate the effect a change would have on the therapeutic agent release profile.

The method of treating a disease or disorder using implantable device 1 includes implanting the device 1 at a target area 3 of an organ or tissue of interest. In some embodiments, the implantable device 1 can be delivered via a needle inserted into the target area 3. In some embodiments, an incision may be made in the surface of the tissue or organ of interest, and the implantable device 1 inserted through the incision and to the target area 3, for example, using a micro stylet. In some embodiments, the incision is about 1 millimeter in length or less, including about 1 millimeter, about 900 micrometers, about 800 micrometers, about 700 micrometers, about 600 micrometers, about 500 micrometers, about 400 micrometers, or about 300 micrometers. The implantable device 1 can be delivered, in some embodiments, using a stereotaxic system and under the guidance of a biomedical imaging modality. Likewise, implantable devices 1 that are configured to be detected by imaging modalities can also be removed using an imaging modality at a later time.

After implantation, a therapeutically effective dosage of a therapeutic agent 8 is locally released from an interior void 4 of the implantable device 1, through a porous outer wall 2 of the implantable device, and into the target area 3. The implantable device 1 enables localized delivery at higher doses than would be possible via systemic delivery. Chemotherapies and nanoparticle-based treatments can be toxic at high systemic dosages, but a high concentration localized delivery may be possible using the implantable devices 1. Additional therapeutic agents can be incorporated into and released from the porous outer wall 2, as described above.

Furthermore, the implantable devices 1 can be custom built to address a particular disease or can be specially designed to treat an individual patient, as described above. In some embodiments, the disease or disorder is a cancer, an ocular disorder, or a neurological disorder, including, but not limited to, Parkinson's disease, Alzheimer's disease, epilepsy, cerebral palsy, autism, or multiple sclerosis. In some embodiments, the disease or disorder is another neurological and/or psychiatric illness such as, but not limited to, obsessive compulsive disorder. In some embodiments, the disease or disorder is a mood disorders such as, but not limited to, bipolar disorder and depression. The target area 3 can be part of any tissue of the body. Certain tissues are particularly complex and have restricted reserves for regeneration and growth. For these tissues, the use of non-obtrusive, local implantation and delivery could be of particular advantage. For example, target area 3 could be located in a complex tissue such as brain tissue and the cerebral spinal fluid, spinal cord tissue, the eyes, tumors, liver, kidney, muscle, musculoskeletal tissues and cardiac tissue and bone marrow. In some embodiments, the implantable device can be made and implanted into the patient within 48 hours of when the individual patient data is gathered. For example, using the technology disclosed herein, it is feasible to image the afflicted target area 3, fabricate a custom-made implantable device 1 based on the appropriate anatomical dimensions in a short time frame (for example, less than 1 hour), have its contents customized according to the therapeutic needs, and implant the device directly to the target area 3, all within a day.

The implantable devices 1 disclosed herein can also be used in methods of screening potentially therapeutic agents for a desired biological response. For example, one or more implantable devices 1 loaded with a potentially therapeutic agent can be implanted into a test tissue. In some instances, multiple implantable devices are loaded into the test tissue. The implantable devices can vary with respect to the type of therapeutic agent they deliver, the dosage of therapeutic agent that they deliver, the release profile of therapeutic agent they deliver, or a combination thereof. The potentially therapeutic agent(s) are locally released from the interior voids 4 of the implantable device 1, through a porous outer wall of the implantable device, and into the test tissue. The test tissue is monitored for responses that are indicative of the therapeutic effectiveness of the potentially therapeutic agent.

In some embodiments, the implantable devices 1 can be utilized in a cellular biopsy procedure. For example, the implantable device 1 may be fabricated with pores large enough for cell migration into the interior void 4. The implantable device is then inserted into a target tissue. After a length of time appropriate to enable cell migration into the interior void 4, the implantable device 1 can be withdrawn. The cells inside the interior void 4 can then be analyzed. In this and other aspects, the use of an autofluorescent material to fabricate the porous outer walls 2 can be advantageous for tracking the device using imaging modalities. Alternatively, traceable materials, such as gadolinium, can be incorporated into the porous outer walls 2 to facilitate tracing via imaging modalities.

A number of embodiments of the invention have been described. Nevertheless, it will be understood that various modifications may be made without departing from the spirit and scope of the invention. Accordingly, other embodiments are within the scope of the following claims.

EXAMPLES

The examples demonstrate the consistency and resolution of the printed implantable devices; the ability to control the elution of materials through the pores; the direct and local delivery into brain tissue; and the stability in placement after delivery into tissues. This strategy has the potential for focal and minimally invasive delivery of desired therapeutic agents into tissues of interest, while also offering flexibility in designing and filling the device dependent on the situational need.

Example 1: An Implantable Microporous Device for Local and Controlled Delivery of Therapeutic Agents Methods Animal Handling: All animals were handled in accordance to protocols approved by the Institutional Animal Care and Use Committee of Children's National Medical Center. All methods were performed in accordance with the relevant guidelines and regulations.

Generation of CAD Design. Solidworks 3D CAD software (Dassault Systémes SolidWorks Corporation, Waltham, Mass.) was used to design and model iterations of the implantable device. Pores were generated by projecting a linear pattern of circles on the inner surface of the implantable device model, revolving the linear pattern around the central axis, and performing an extrude cut feature to remove material equivalent to the wall thickness. The model is exported as a binary stereolithography (STL) file for 3D printing. A deviation tolerance of 0.50 µm and angular tolerance of 10 degrees was chosen to preserve resolution during fabrication. The implantable device was designed with a total of 10,140 pores on its exterior. For elution experiments, the implantable device with ¼ holes were designed with a total of 2,550 pores.

Fabrication of the implantable devices. Implantable devices were printed using the Nanoscribe Photonic Professional GT 3D Laser Lithography system (Nanoscribe GmbH, Eggenstein-Leopoldshafen, Germany). The printing file was prepared using DeScribe software (Nanoscribe GmbH), and printing was performed using Nanowrite software (Nanoscribe GmbH). Photoresists used were IP-Dip printed on fused silica glass substrate (for the 63× objective) and IP-S on ITO-coated soda-lime glass (for the 25× objective) (Nanoscribe GmbH). Photoresist was drop-coated on substrates cleaned with 99% acetone, 99% isopropyl alcohol, and ddH2O, and was placed directly in contact with the objective using Dipin Laser Lithography (DiLL) printing mode. Printing was done with a printing speed of 20,000 µm/s at a laser power of 35 mW. After printing, the samples were post-processed in propylene glycol monomethyl ether acetate (PGMEA) for 30 min to remove excess uncured photoresist, washed with 99% isopropyl alcohol, and air-dried. The PPF fabrication proceeded as previously published.

Imaging and Sample Processing. Scanning electron microscope imaging (SEM) was done using a Hitachi S-3400N (Hitachi, Tokyo, Japan). Optical imaging was done using a Leitz Wetzlar Ergolux model 020-488.026 (Leica, Wetzlar, Germany) using the TSview7 software (Xintu Photonics, Fujian, China) and was utilized for measuring the dimensions for the implantable device. Pore diameters were measured for both a horizontal and vertical measurement and averaged. Vertical pore spacing was measured by finding the distance between the center of one pore and the center of the vertically adjacent pore. For these measurements, 10 measurements were made for every tube, after which an average measurement was calculated and compared to other tubes.

Filling of implantable devices. Implantable devices were loaded with the aid of a stereotaxic apparatus (Kopf Instruments, Tujunga, Calif.) and a pulled 1×90 mm glass capillary (Narishige, Tokyo, Japan). The tip of the pipette was broken and attached the stereotaxic apparatus parallel to the barrel of the implantable device. To fill implantable devices with agarose solution, 2% agarose in PBS was first melted and diluted to room temperature PBS at a final concentration of 0.35%. This solution was loaded into the pulled glass pipette and stereotaxically inserted into the barrel of the implantable device. Its contents were then released into the chamber of the device via a Picospritzer (Parker, Hollis, N.H.), after which the mold was allowed to dry and solidify. Implantable devices were subsequently capped with cyanoacrylate adhesive to seal their contents.

Elution Experiments. To determine the elution of molecules from the implantable device, 50 nm Fluospheres Fluorescent Microspheres (Thermo Fisher Scientific, Waltham, Mass.) were mixed with the 0.35% agarose solution and loaded into devices without the 40 µm bases attached to silica glass. The molds were allowed to solidify and dry, and implantable devices were subsequently capped with cyanoacrylate adhesive to seal its contents. Filled devices were then placed in a 60 mm Petri dish and submerged in 5 mL of PBS to allow for elution. Fluorescence was captured using an Olympus FV1000 (Olympus, Tokyo, Japan) confocal microscope at the indicated times within PBS, and relative fluorescence intensity was determined using ImageJ software. Percent (%) Relative Fluorescence Intensity was calculated by the relative fluorescence intensity of the tube contents at the indicated time point divided by the relative fluorescence intensity of the tube contents at 30 minutes times 100%.

Ex vivo implantation and Mechanical Stress Testing. For ex vivo implantation tests, adult wild-type C57BL/6 mice (The Jackson Laboratory, Bar Harbor, Me.) were sacrificed, with the top of the skull removed to expose the cerebral cortex. The stylet of a 22-gauge needle was used to puncture a small opening in the cortex. Implantable devices filled with 0.35% agarose were then placed into the cortical regions. For mechanical stress testing, ex vivo mouse brains with implanted devices were placed in 50 mL conical tubes. Tissue with the implantable device was first fixed overnight with 4% paraformaldehyde in PBS, and then subsequently washed in PBS 3 times 10 minutes each. The conical tubes were then filled with 40 mL of PBS and placed on an orbital shaker at 60 rpm continuously for 7 days. Brightfield and fluorescence imaging of the implantable devices were done using a Zeiss SteREO Discovery V8 microscope (Carl Zeiss, Oberkochen, Germany).

In vivo implantation. For in vivo implantation, adult C57BL/6 mice were anesthetized with ketamine/xylazine (100/10 mg/kg). The skull was exposed with a sterile scalpel, and the brain exposed with a surgical drill with a 0.7 mm diameter burr (Fine Science Tools, Foster City, Calif.). Cortical brain tissue was pierced with the stylet of a 22 gauge needle, after which the implantable device was inserted directly into the pierced region. After implantation, animals were allowed to recover.

In vivo release. Implantable devices were filled with α-bungarotoxin fused to the dye Alexa Fluor 555 (α-BTX Alexa 555) in PBS at a concentration of 0.3 mg/mL. Animals were treated with the implantable device for 2 hours prior to sacrifice. Tissues were prepared for live cell electrophysiology assays (patch clamp) and fluorescence imaging.

Results

The design of the implantable device: a small device for direct and controlled therapeutic delivery. Given the varied needs for direct pharmacological delivery to diseased and afflicted tissues, particularly in complex organs like the brain, a method is needed to provide maximal versatility in terms of the design of the device, the materials utilized for the build, and the agents released. This example demonstrates the design of an implantable device that (1) was capable of holding therapeutic agents in a fixed container; (2) can release agents over time based on the design of the tool, materials used in its production, and contents of the device; (3) is able to be tailored according to different situational needs; and (4) is local in its direct effect.

Based on these criteria, a hollow cylinder was developed with perforated holes on the exterior designed for the delivery of therapeutic agents for precise and controlled release (FIG. 1a). The device is small enough to fit inside a 22-gauge needle (FIGS. 1b and c) to allow for direct delivery. To use, the device is filled with the therapeutic agents of interest, capped, and implanted directly into a target tissue (the mouse cerebral cortex, in this example), whereupon the contents are eluted to the surrounding target area (FIG. 1d).

Figure 2:
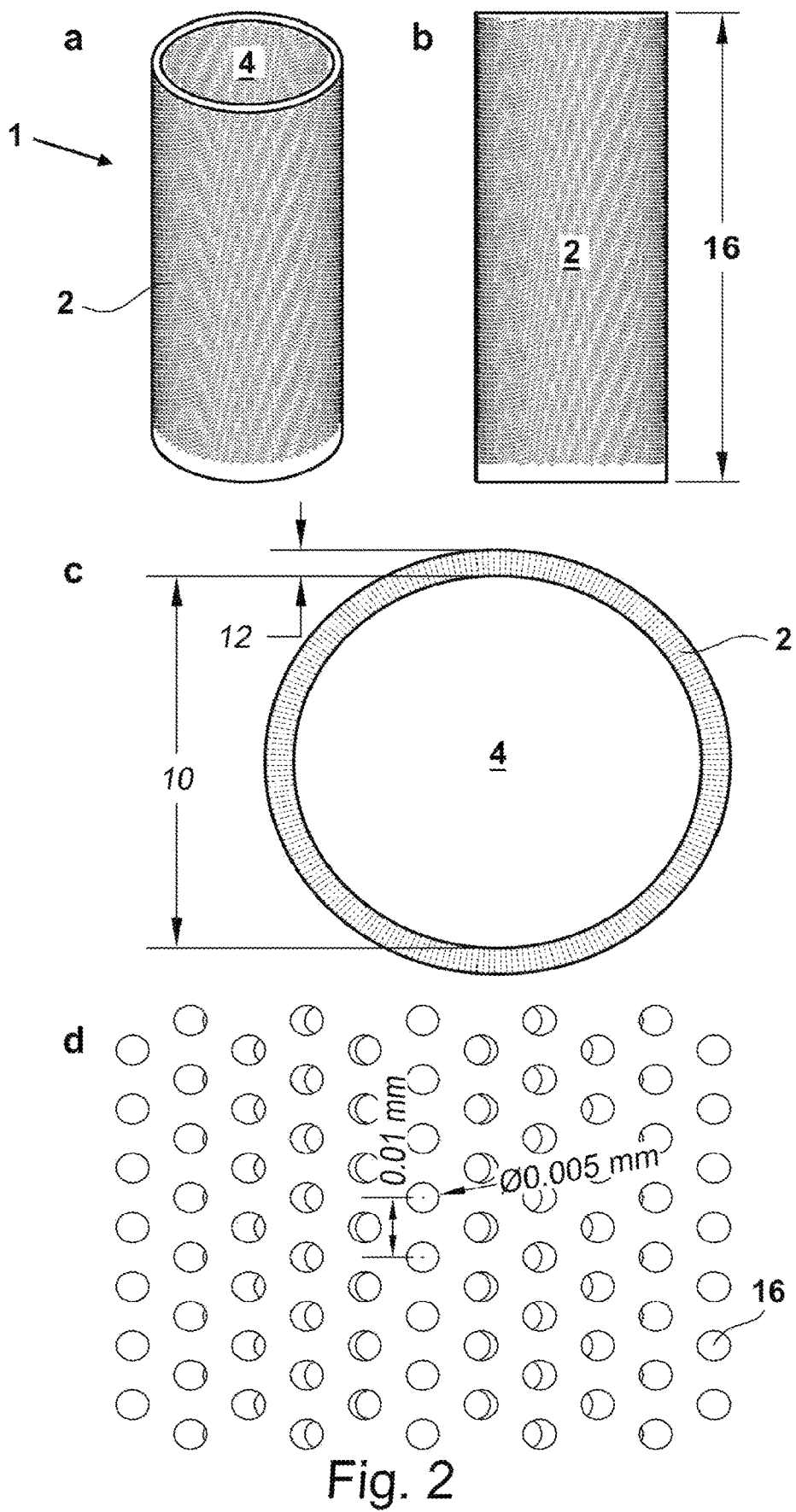
FIGS. 2A-2D show the CAD design for the implantable device. (a) Oblique angle view of the implantable device. Its design is a 300 µm empty hollow inner diameter to be filled, a 20 µm outer wall, a 40 µm solid base, and a 900 µm total height. The outer wall is perforated with holes, each with a diameter of 5 µm. (b) Side profile of the implantable device. (c) Top profile of the implantable device showing the holes perforating through the outer wall. (d) Higher magnification of pores of the implantable device showing dimensions.

The design of the implantable device of Example 1 includes a 300 µm hollow inner diameter, a 20 µm outer wall, a 40 µm solid base, and a 900 µm total height (FIG. 2). The inner diameter was made as small as possible to allow for minimal invasiveness while still being feasibly able to be filled (see FIG. 6), while the outer wall thickness was made as thin as possible while still retaining the structural integrity of the device. Here, the height was determined to be similar to the thickness of the mouse cerebral cortex (FIGS. 2a and b). The cylindrical shape will facilitate delivery using a standard syringe and needle, as well as mimic the alignment of cortical columns (FIG. 2c). The outer wall is perforated with holes with a diameter of 5 µm to facilitate the elution of materials from the device into the surrounding tissue while preventing cells from migrating to the inside of the device (FIG. 2d).

Figure 3:
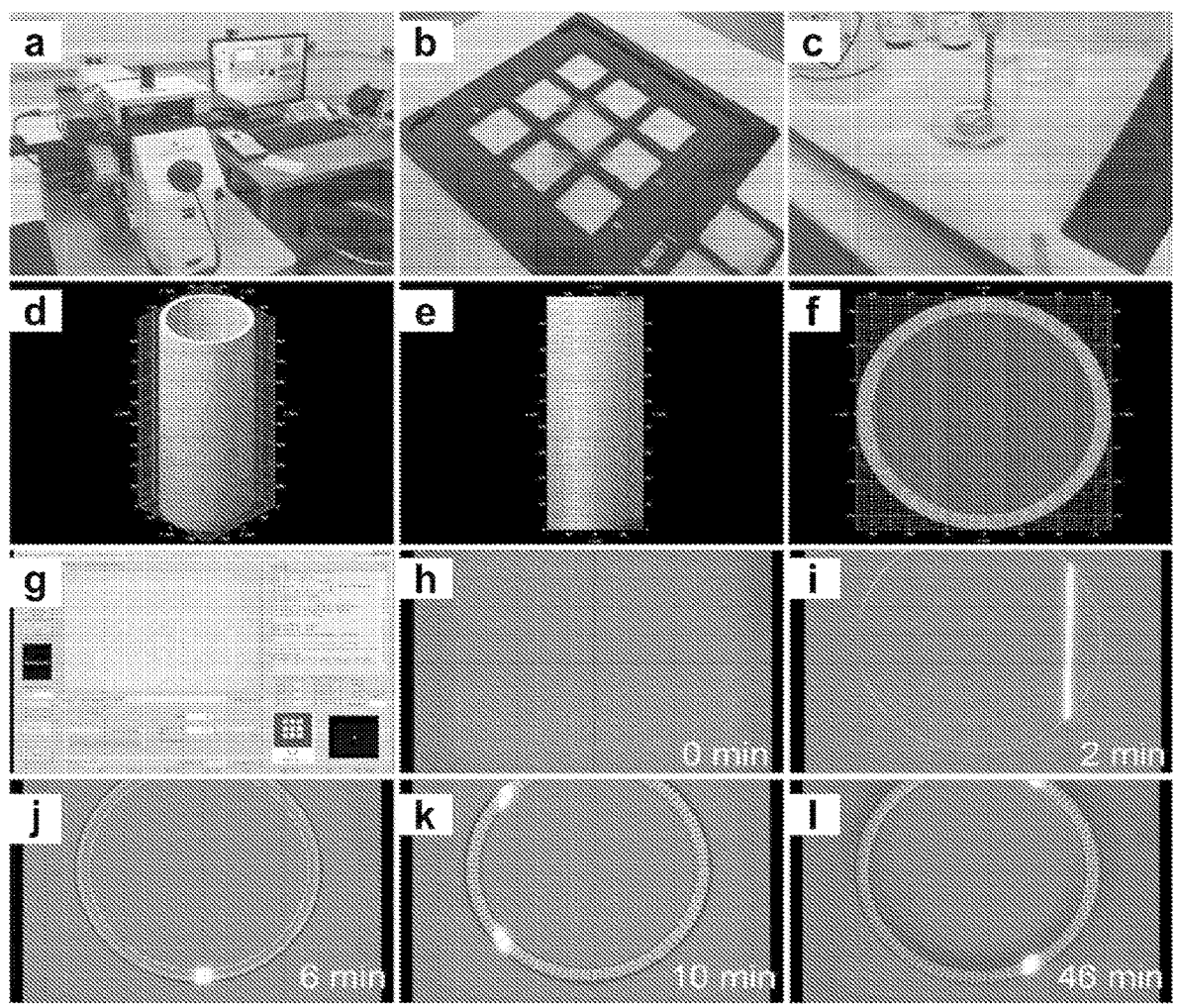
FIGS. 3A-3L show the production of the implantable device using a Nanoscribe lithography system. (a-c) Printing and development of structures using the Nanoscribe system. Implantable devices were printed using the Nanoscribe system (a). Photoresist was drop-coated onto the substrate for printing (b), and was afterwards developed in PGMEA (c). (d-f) DeScribe renderings of the implantable device prior to printing on the Nanoscribe. The renderings show the structures to be rendered (d-f). (g) Initial setup screen for Nanoscribe printing using the Nanowrite software. (h-l) Time lapse imaging of the implantable device being printed at various time points from the start of printing (h) to final completion (l). The base of the implantable device is observed at 2 minutes into printing (i). The inner wall is then constructed at 6 minutes into printing (j). By 10 minutes of printing, the pores of the Implantable device begin to be observed (k). The total time of making one implantable device is approximately 46 minutes (l).

Fabrication of the implantable device. 3D printing was used to fabricate the implantable device because it provides adaptability with regards to the materials utilized for printing and the designs that can be made (FIG. 3). The Nanoscribe Photonic Professional GT 3D laser lithography system, a maskless two-photon polymerization (2PP) 3D printer (FIG. 3a-c), was used to make the implantable devices of Example 1. The implantable device was printed directly on a glass substrate with either the photoresist IP-Dip or IP-S (FIG. 3b), after which the cover slip was processed in propylene glycol monomethyl ether acetate (PGMEA) to remove residual materials and subsequently dried (FIG. 3c). The Nanoscribe system is powerful in its ability to resolve configurations of a wide range, particularly its ability to print structures several hundred microns tall at micron-level resolution (FIG. 3d-f). The implantable device was constructed from the bottom-up, with the base of the tube printed first, followed by the walls with the perforated holes (FIG. 3g-I). For the final build, using the photoresist IP-S with a 25× objective, the total fabrication time was finished at 46 min (FIG. 3I).

Figure 4:
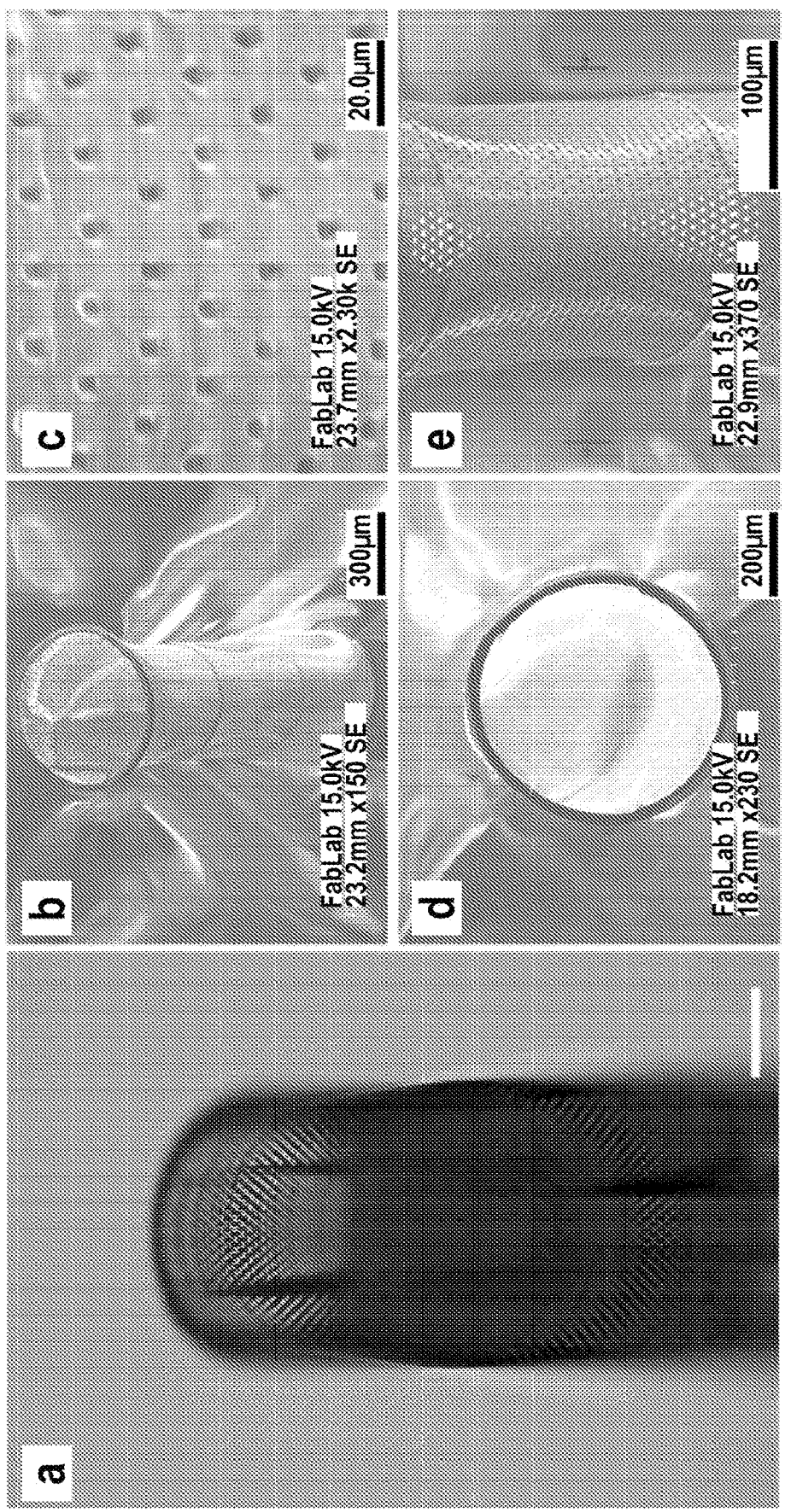
FIGS. 4A-4E show a prototype of the implantable device. (a) Oblique light microscope image of the Implantable device prototype made with IP-Dip using a 63× objective. The light scattering makes it possible to see the finer features of the device. (b-e) SEM images of the implantable device prototype. Many of the features, including the hollow tube and holes (b and c) are present. However, certain aberrations and stitching in printing, including on the rim (d) and wall (e), were present. Scale bars for a, b, d, and e=100 µm. Scale bar for c=10 µm.

Build and consistency of the implantable device. The initial prototypes utilized the photoresist IP-Dip with a 63× objective for printing, which provided a higher resolution print of the device at the cost of efficiency of printing (FIG. 4). Imaging via light microscopy (FIG. 4a) and scanning electron microscopy (SEM) (FIG. 4b-e) showed several of the major features to be present, including the 5 µm holes (FIG. 4c). However, some aberrations were observed including imperfections along the sides and rim of the implantable device and a slight warping of the walls (FIGS. 4d and e).

Figure 5:
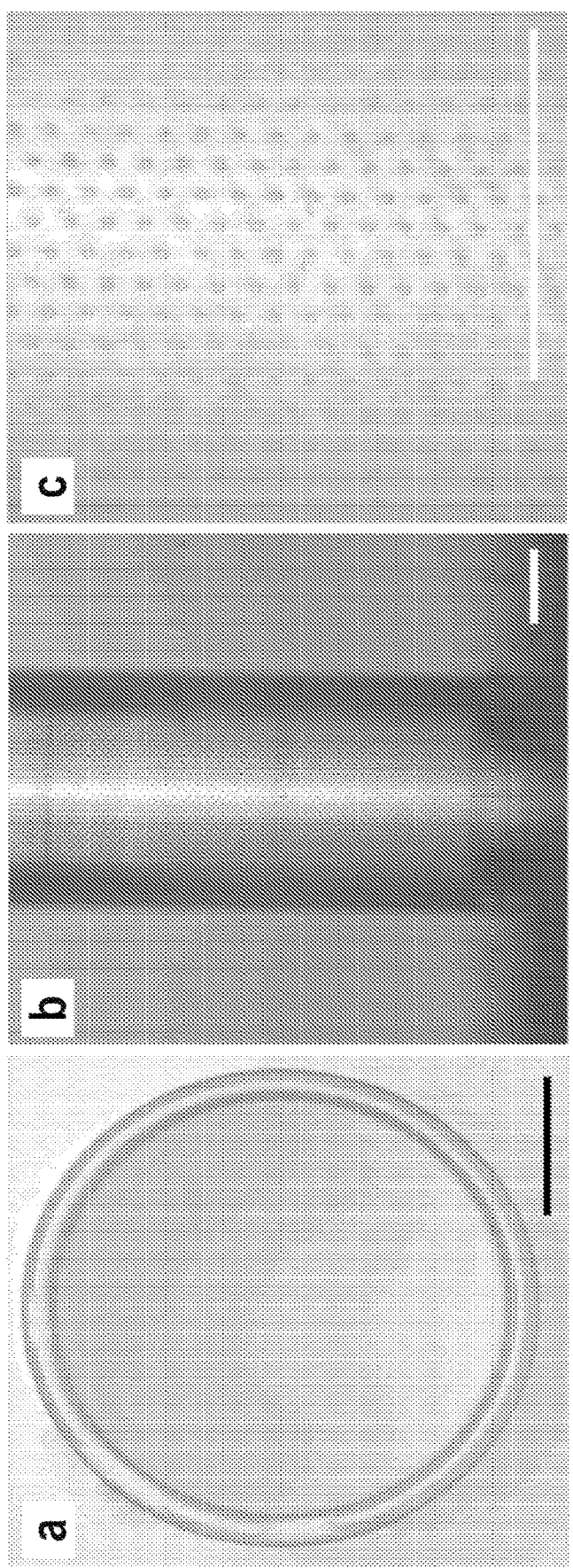
FIGS. 5A-5C show light microscopy images of final implantable device. (a) The top view shows precision of the wall structure of the device. (b) The side profile showing the width and base of the structure. (c) Further magnification of the walls shows the fine pore structures of the device. Scale bars=100 µm.

To eliminate these variations, another condition was tested which was better suited for printing of larger structures, utilizing the photoresist IP-S with a 25× objective (FIG. 5). As the sensitivity of the IP-S material did not allow SEM imaging, optical microscopy was utilized for imaging and measuring the device. With this printing method, implantable devices displayed no obvious structural imperfections (FIGS. 5a and b) and also retained the finer features (FIG. 5c). These devices showed high levels of consistency with respect to structural integrity and features between builds (see Table 1). Several of the fine features of the device, including pore diameter (Actual: 4.827±0.3938 µm; Design: 5.000 µm; n=3 devices, 10 holes per device), vertical spacing of pores (Actual: 10.64±0.3938 µm; Design: 10.00 µm; n=3 devices) and wall thickness (Actual 21.41±1.692 µm; Design: 20.00 µm; n=5 devices) were consistent to the original design. Macro-dimensions such as the inner diameter (Actual: 307.6±5.644 µm; Design: 300.00 µm; n=5 devices), outer diameter (Actual: 350.4±6.271 µm; Design: 340.0 µm; n=5 devices), and height of the devices (Actual: 964.0±9.167 µm; Design: 900 µm; n=3 devices) showed consistency between devices, but were slightly larger than the original design.

TABLE 1

Implantable device physical dimensions versus the original design.

| | Actual (µm) | Designed Value (µm) |
|---|---|---|
| Pore Diameter | 4.827 ± 0.3938 | 5.000 |
| Vertical Spacing | 10.64 ± 1.969 | 10.00 |
| Wall Thickness | 21.41 ± 1.692 | 20.00 |
| Diameter (Inner) | 307.6 ± 5.644 | 300.0 |
| Diameter (Outer) | 350.4 ± 6.271 | 340.0 |
| Height | 964.0 ± 9.167 | 900.0 |

Figure 6:
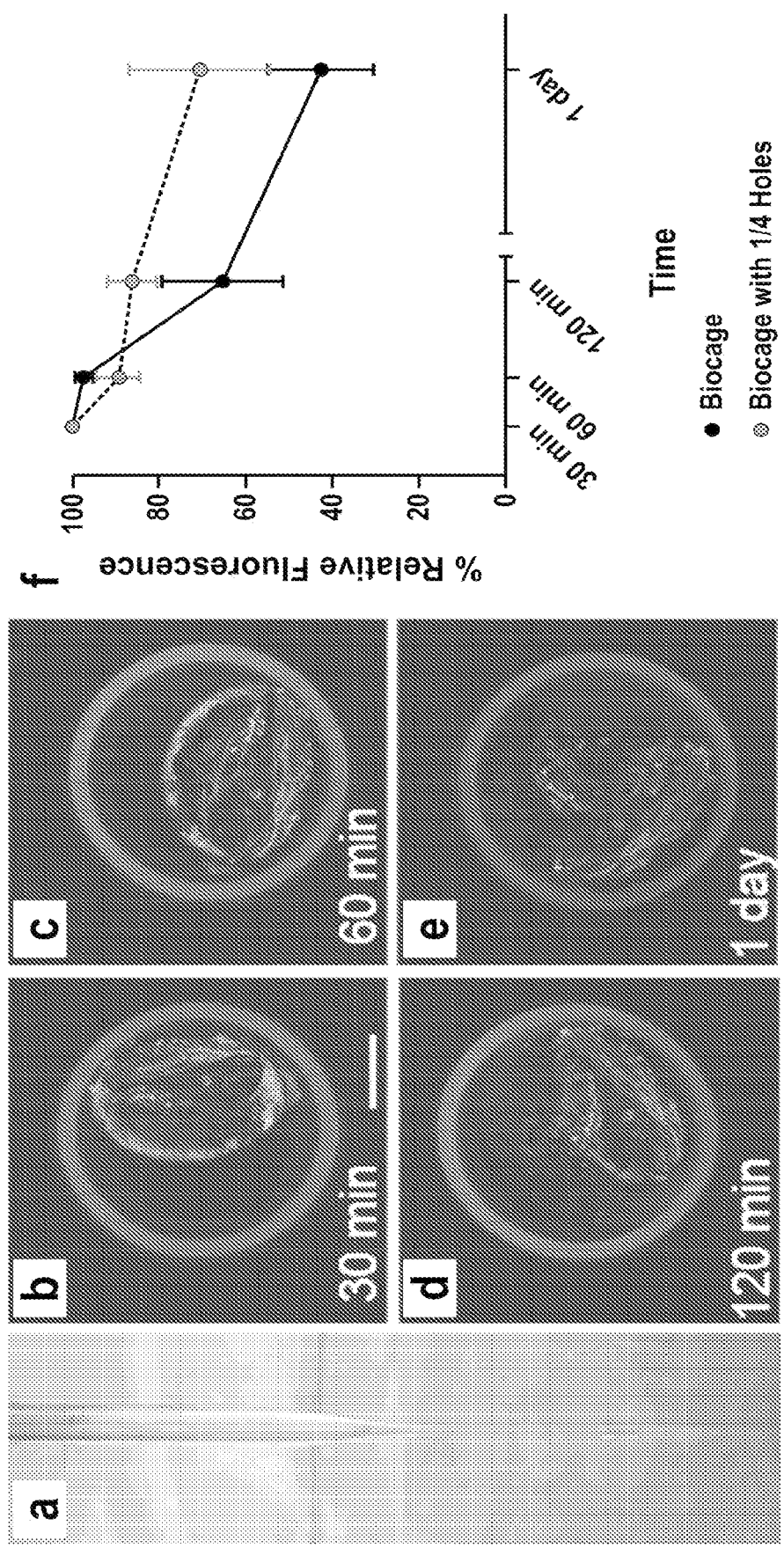
FIGS. 6A-6F demonstrate the elution of materials through the implantable device. (a) Loading of the implantable device using stereotaxic device and a filled glass pipette. Implantable devices were filled with fluorescent microspheres at a 1:1000 concentration within a 0.35% agarose solution and allowed to solidify, and sealed with cyanoacrylate adhesive. (b-e) Elution of fluorescent microspheres from the implantable device. Devices attached to silica glass without bases are filled with fluorescent microspheres in agarose, and put into PBS to demonstrate elution. Beads are imaged using an inverted confocal microscope at equal laser power and exposure times. A reduction of fluorescence is observed, indicating elution of the microspheres. Implantable devices are autofluorescent, but begin lose this fluorescence when exposed to PBS over extended periods. Scale bar=100 µm. (f) Quantification of relative fluorescent values demonstrating elution in both the implantable device (blue) and an implantable device with ¼ of the number of pores (red). Relative fluorescent values are shown in relation to the initial measure at 30 min in PBS. Elution rates are observed in relation to the relative number of pores in the device, with fewer pores resulting in an overall slower rate of elution. Error bars in SEM. n=4 per time point.
Figure 7:
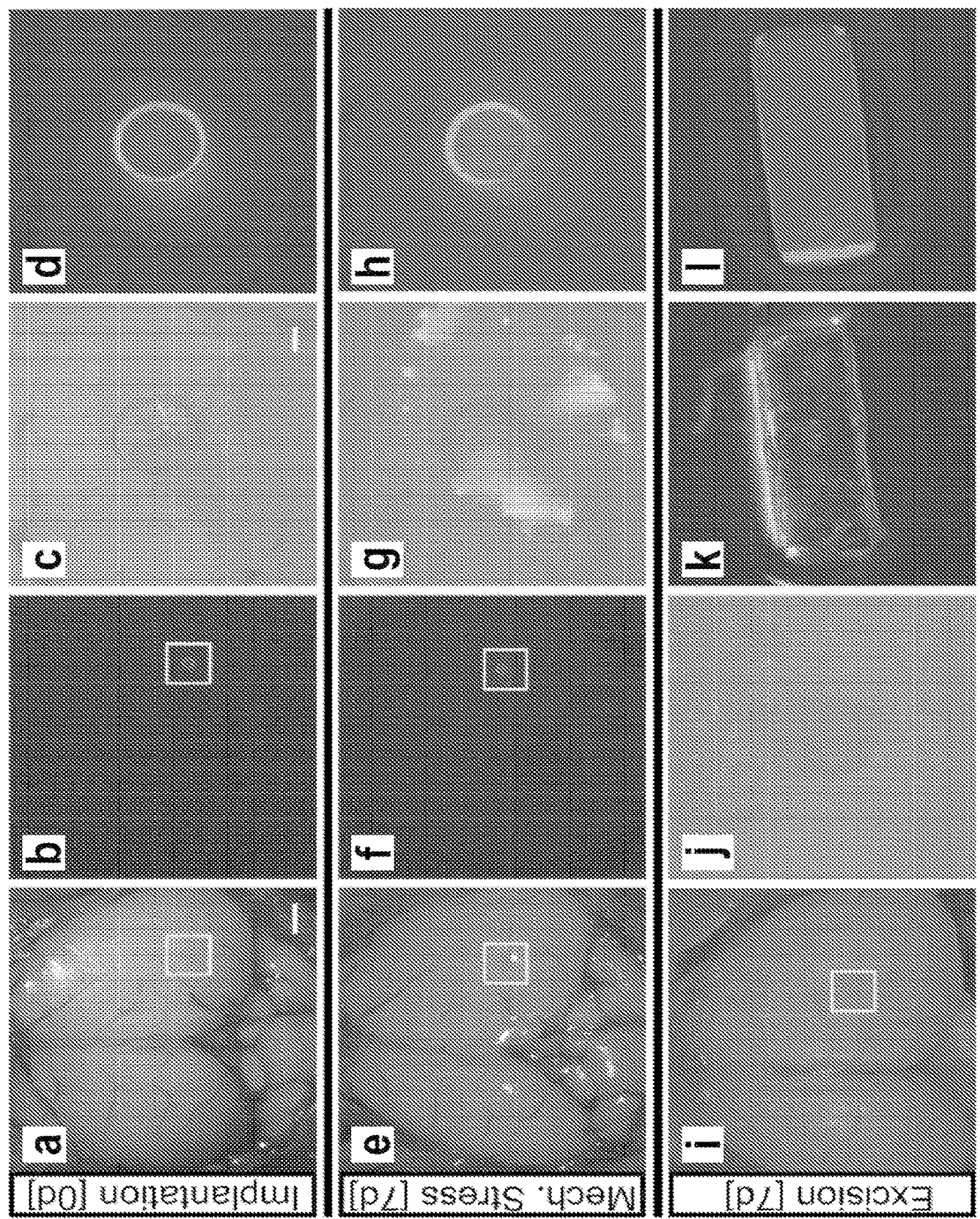
FIGS. 7A-7L show the implantation, mechanical stress, and excision of implantable device in the ex vivo mouse brain. (a-d) Implantation of an implantable device. Light (a and c) and fluorescent (b and d) images showing the device in comparison to the rest of the brain. Implantable devices were filled with 0.35% agarose prior to implantation into ex vivo mouse cortex. c and d are higher magnification views of the areas denoted by yellow boxes in a and b, respectively. n=3/3 brains successfully implanted. (e-h) Light (e and f) and fluorescent (g and h) images of implanted devices after 7 days of mechanical stress of the same brain shown in (a-d). Following implantation, brains were fixed with 4% paraformaldehyde overnight to prevent tissue decay, and shook on a circular rocker for a period of 7 days. Implantable devices were still present within the tissue without movement seen from site of implantation (compare a and b to e and f). g and h are higher magnification views of the areas denoted by yellow boxes in e and f, respectively. n=3/3 brains. (i and j) Excision of the implantable device from the tissue. Implantable devices are successfully excised from the tissue (l) without displaying additional damage to the brain (j). j is a higher magnification of the area denoted by the yellow box in i. (k and l) Light (k) and fluorescent (l) images of implantable devices after mechanical stress and removal. Implantable devices remained wholly intact after stress and removal. n=3/3 implantable devices successfully excised. Scale bar for a and b, e and f, i=1 mm. Scale bar for c and d, g and h, k and l=100 µm.

Elution of small molecules through the implantable device. Next, the efficacy of the implantable device to elute material through its pores (FIG. 6) was evaluated. Implantable devices were filled directly with warmed agarose (an inert polysaccharide hydrogel) mixed with stable 50 nm fluorescent microspheres via a pulled glass pipette and stereotaxic apparatus, after which the contents were dried and the tubes capped with cyanoacrylate adhesive (FIG. 6a).

To determine the elution, the relative amount of fluorescence within the agarose gel in the implantable device devices soaked in phosphate buffered saline (PBS) was measured over a period of time (FIG. 6b-e). To observe the fluorescence of these molds directly via confocal microscopy, devices in this experiment were printed without the 40 µm base and were directly attached to silica glass to allow for imaging. The agarose within these devices showed a consistent reduction in fluorescence intensity through a 1 day period relative to their original intensity measured after 30 min in PBS (FIG. 6f), indicating the gradual elution of the microspheres through an extended period of time from the designed pores. When applying the same experiment to implantable devices with approximately ¼ of the number of pores, the reduction of fluorescence intensity was diminished, indicating that slower elution has occurred (FIG. 6f). Together, the data indicate that the implantable device is capable of eluting small molecules over a controlled period of time.

Ex vivo implantation and stability of the implantable device. Next, the stability of the implantable device and its ability to withstand stressors during implantation and within tissue was evaluated (FIG. 7 and FIG. 8a-d). Prior to implantation, devices were filled with warmed agarose solution and allowed to solidify, which would both act as a carrier for desired molecules as shown in the elution experiments (see FIG. 7) and provide additional stability for the device to be manipulated. Implantable devices were then transplanted into ex vivo adult mouse brains by first perforating the dura and cortical tissue using the stylet of a solid 22-gauge needle, then inserting the device directly into the perforation. Direct and focal implantation was observed into the mouse brain without difficulty (n=3/3 successful implanted devices); in addition, the device could be tracked through fluorescence microscopy given the auto-fluorescent properties of the material (FIG. 7a-d).

Figure 8:
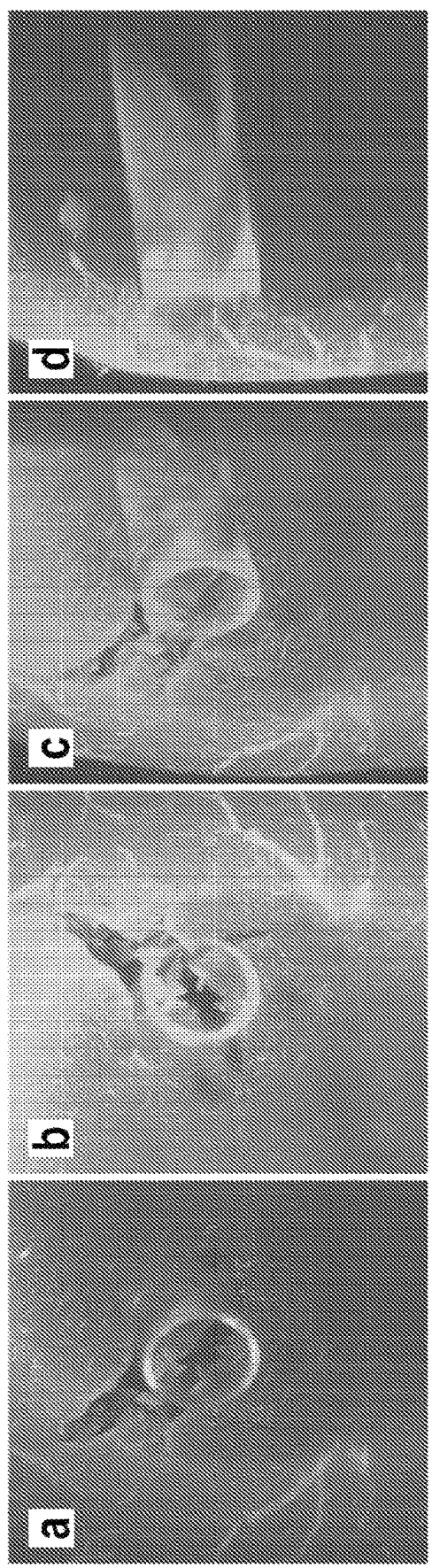
FIGS. 8A-8D show the imaging of the implantable device in the ex vivo brain. (a) A collapsed stack of images (1 mm thick) from a multiphoton microscope, showing the implantable device implanted in ex vivo brain tissue after undergoing mechanical stress on a circular rocker for 7 days. (b-d) 3-dimensional reconstruction of the implantable device within ex vivo brain tissue showing that the implantable device can be imaged within tissue.

After successful implantation, the question of whether the device could withstand other forces within the tissue was evaluated. In order to apply forces within the tissue that would mimic mechanical stressors experienced in vivo, the implanted ex vivo mouse brains were placed in 50 mL conical tubes and shaken on an orbital shaker at 60 rpm continuously for a period of 7 days. The vigorous shaking was done to ensure the safety of the device even when the brain was under such physical duress. After this period, the devices were found within the implanted areas, without any observable deficits (FIG. 7e-h, n=3/3 evaluated implanted brains). This was further evaluated by excising the devices from the tissue and observing both the implantation site and the device itself. Implantable devices were easily removed, with clear and focal implantation sites observed in the ex vivo brains (FIGS. 7i and j; n=3/3 implanted brains). In addition, the implantable devices were wholly intact without observable damage, demonstrating the robustness of the device for transplantation (FIGS. 7k and l; n=3/3 excised implantable devices). FIG. 8a is a collapsed stack of images (1 mm thick) from a multiphoton microscope, showing the implantable device implanted intact in the brain tissue after applying mechanical stress. FIGS. 8b-d show 3-dimensional reconstructions of the implantable device within ex vivo brain tissue. Fluorescent imaging was possible due to auto-fluorescent properties of the materials used to fabricate the implantable device.

Figure 10:
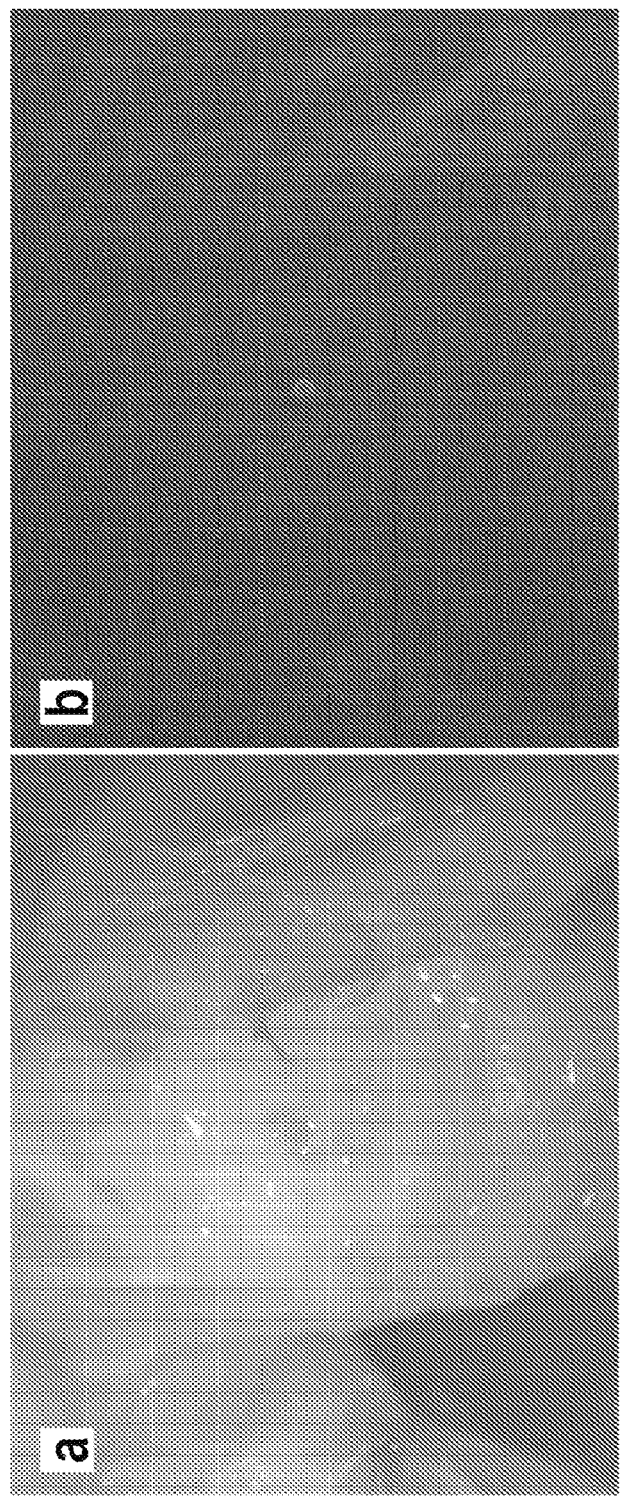
FIGS. 10A-10B show an implantable device still within the brain after 24 hours of implantation in vivo. (a) Perfused mouse skull and brain showing the original site of implantation. A small section of skull was exposed via a surgical drill, after which the brain was pierced with the stylet of a 24 gauge needle, after which the implantable device was then inserted into hole. The animal was then allowed to recover and sacrificed 24 hours after surgery. (b) Fluorescence image of (a) displaying the implantable device within the brain.
Figure 11:
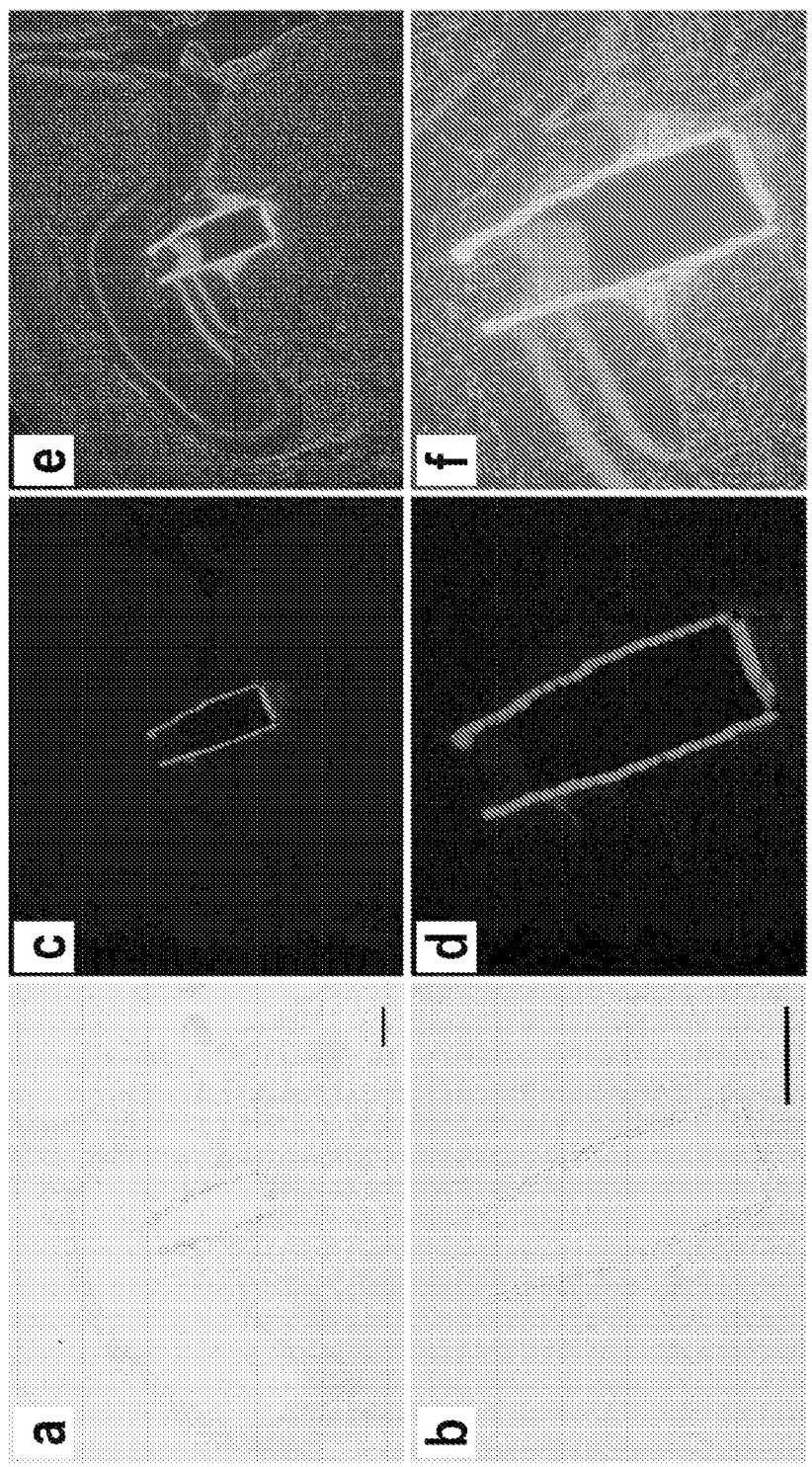
FIGS. 11A-11F show sections of the brain tissue 24 hours after implantation of the implantable device, demonstrating that the implantable device remained intact. (a and b) Low (a) and high (b) magnification light microscope images showing the uncapped implantable device intact within the hippocampus. The device remains wholly intact and is capable of being cryosectioned 24 hours after in vivo implantation. (c and d) Green fluorescence image of (a) and (b) respectively of the device. (e and f) Nuclear staining via DAPI showing the implantable device. While tissue is observed coming from the uncapped region, no cells are visible through the pores of the device. Scale bars=300 µm.

In vivo implantation. Next, the effects of the implantable device after in vivo delivery were determined. The implantable devices were implanted into the cortex of live mice for 24 hours, after which the mice were euthanized and perfused. FIGS. 10a and 10b show the implantable device still implanted in the brain after 24 hours in vivo. Sectioning of the brain tissue revealed that the implantable device remained intact (FIGS. 11a-11e).

Figure 12:
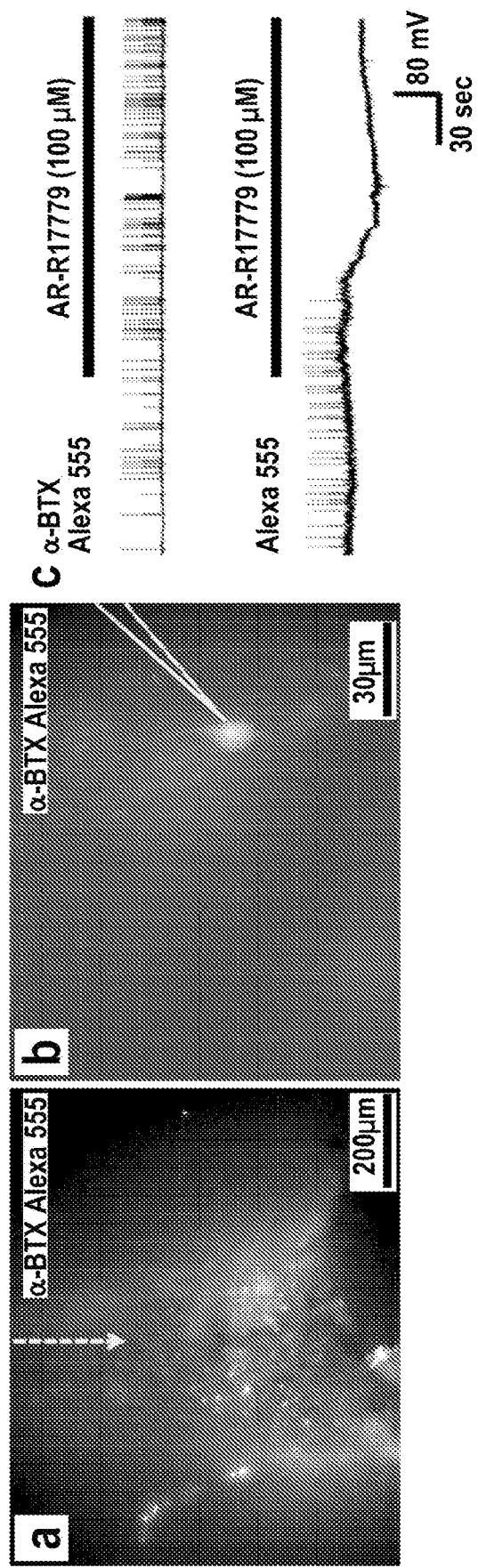
FIGS. 12A-12C demonstrate that the implantable device is capable of localized release eliciting physiological effects. (a and b) Alexa Fluor 555 was found adjacent the implantation site in the adult mouse cortex, labeling individual cells, indicating uptake of fluorescent α-bungarotoxin (α-BTX). The yellow dotted arrow in (a) denotes the site of implantation. The implantable device here has been dislodged upon sectioning for electrophysiological analysis. The yellow cone in (b) denotes the representative cell that was patched for the graphs of FIG. 12C. (c) Graphs of electrophysiological recordings of cells labeled with α-BTX-Alexa 555 or with control (Alexa 555) after release from the implantable device, confirming delivery and cell viability. Treatment with the agonist AR-R17779 shows no activity in the α-BTX cell while showing inhibitory activity in the control group.

In vivo release. Implantable devices filled with fluorescently labeled α-bungarotoxin (α-BTX) were implanted and the release was studied via imaging and live cell electrophysiology assays. In FIG. 12A, the yellow dotted arrow denotes the site of implantation. Fluorescence was found to be local to the implantation site. FIG. 12B shows that individual cells were clearly labeled, indicating uptake of α-BTX. FIG. 12C shows electrophysiological recordings of cells labeled with α-BTX-Alexa 555 or with control (Alexa 555) after release from the implantable device (patched cell marked with yellow cone in FIG. 12B). The contents of the implantable device were successfully delivered and cell viability was preserved. Treatment with the agonist AR-R17779 shows no activity in the α-BTX cell while showing inhibitory activity in the control group, demonstrating that the released drug is effective.

Figure 13:
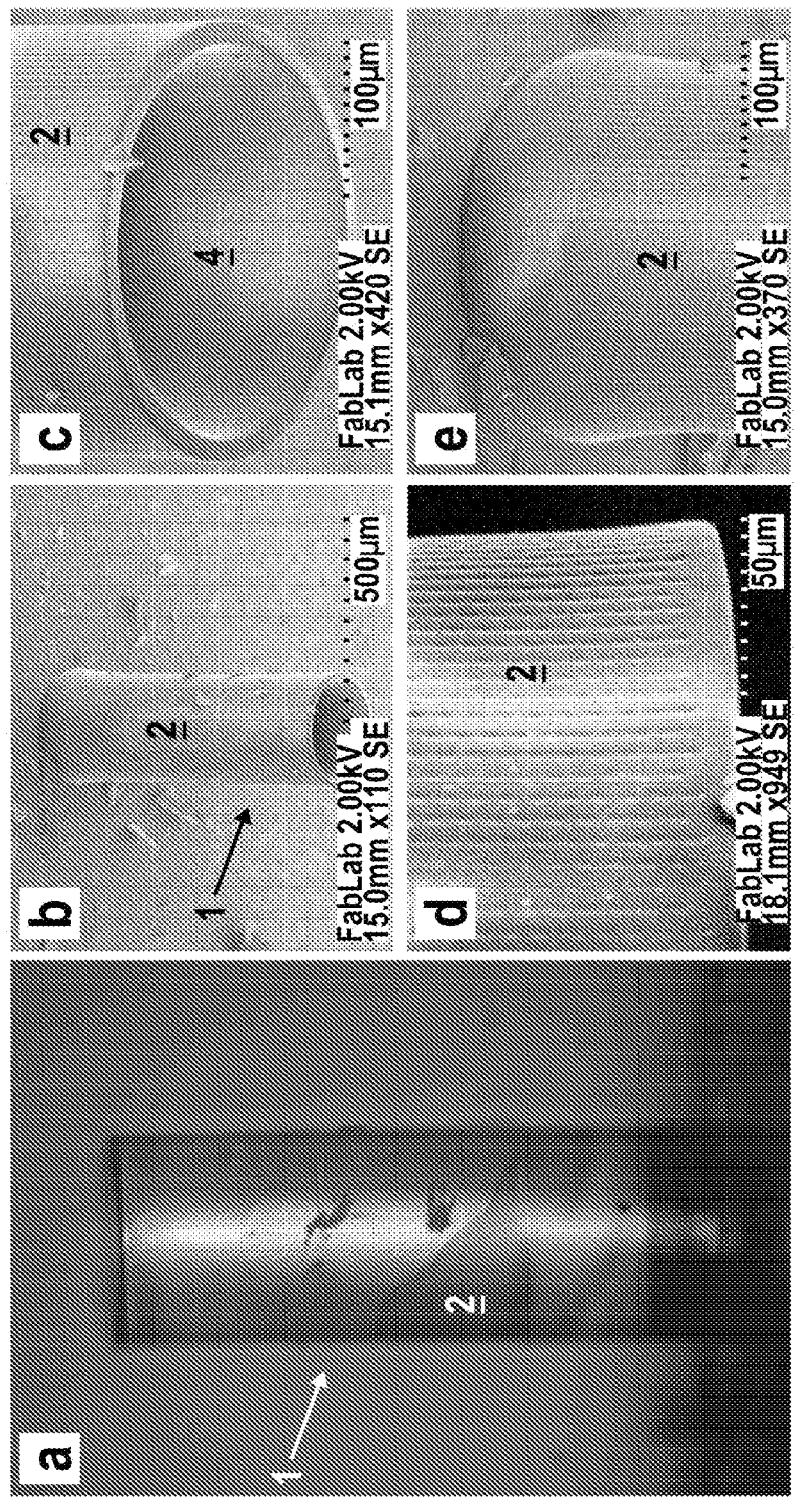
FIGS. 13A-13E show an implantable device fabricated with a biocompatible material, PPF. (a) Low magnification light microscope image of the implantable device. (b-e) SEM of the implantable device made with PPF displaying the hollow tube (c), holes (d) and base (e) are shown.

Fabrication of the implantable device with biodegradable materials. Next, the question of whether the implantable device could be fabricated using biocompatible and biodegradable 2PP crosslinkable materials was addressed. Poly (propylene) fumarate (PPF) was selected as an exemplary biodegradable material for proof of concept purposes (FIG. 13). Light microscope pictures show the implantable device made with PPF to be wholly intact (FIG. 13a). Higher resolution and magnification imaging via SEM shows that the implantable device made with PPF retained the device features including the hollow core, outer pores, and base (FIG. 13b-e).

Discussion

Example 1 reports the fabrication, functionality, and implantation of the implantable device, a porous microcontainer designed for focal and precise delivery of therapeutic agents into tissues. The implantable device is constructed using a high-resolution 2PP laser lithography system that allows a range of printing of features at high resolution from sub-micron to millimeter scale. The data described above demonstrates that the device can be filled and can elute substances through its pores in a controlled manner. Finally, the structural integrity of the implantable device enables it to be directly implanted into brain tissue in a precise manner. The structural integrity is maintained even after experiencing external forces for an extended period of time.

Patients with certain diseases and disorders would find particular benefit from devices able to locally deliver precise and controlled treatments. Utilizing high resolution 3D printing technology on a micron scale, as demonstrated here, provides a unique opportunity in creating customizable devices that can precisely deliver therapies with direct and pinpoint accuracy, for example, to patients suffering from neurological disorders and injuries, ocular diseases, and cancers. Precise local delivery of therapeutic agents can potentially maximize the necessary beneficial effects that would otherwise be toxic or unsafe depending on the context of the therapy. For instance, utilizing higher concentration doses of therapies that would otherwise be toxic for treatments in small volumes with the implantable device may be possible, such as chemotherapies or nanoparticles, by exposing the target of interest directly with the agent of interest while limiting its effects within other body systems.

The implantable devices described herein have the potential for targeted delivery of restorative therapies to the central nervous system (CNS), in which current therapeutic limitations are related to the challenges posed by the complexities of the CNS and its restricted reserves for regeneration and growth. It could be beneficial to deliver neuromodulatory agents to the CNS to moderate brain development and function by altering neurobiological phenomena. However, saturation of the CNS with neuromodulatory agents by systemic application will not achieve the neural network dynamics needed (that is, for targeting specific nodes relative to the rest of the system). The implantable devices described herein would facilitate targeted delivery of neuromodulatory agents to specific nodes in the CNS. This, along with current advances in stereotactic neurosurgical techniques and intraoperative advanced imaging, has the potential for the highly precise delivery of implants into specific areas within the brain. Focused invasive interventions may help bridge these biological distances especially if specific defective "nodes" in an extensive neural network are targeted.

Figure 9:
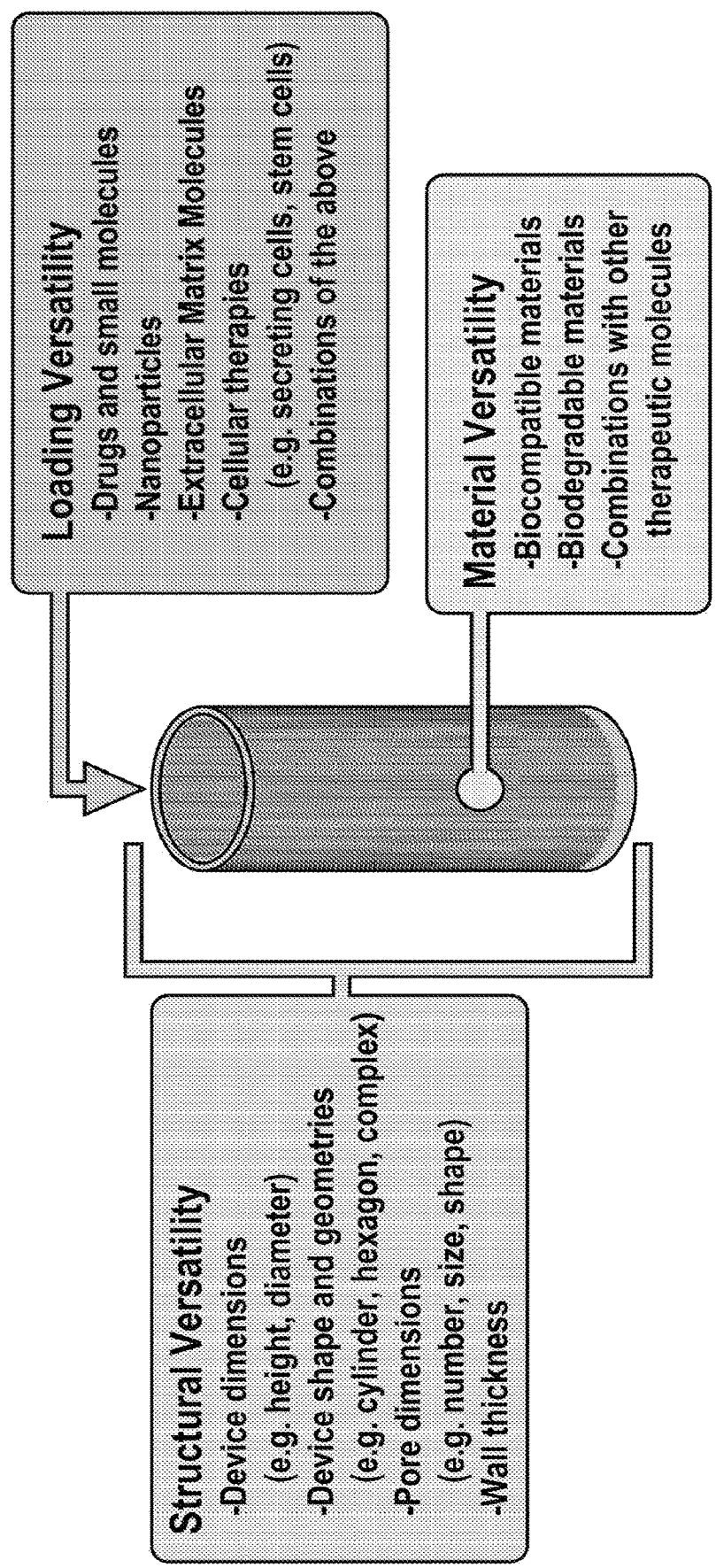
FIG. 9 is a schematic showing the versatility of the implantable device. Several attributes of the implantable device can be easily modified given its design and production for personalized use. Structural versatility comes in the form of attributes of the design including the length, diameter, and shape of the device. Material versatility is possible through different materials that can be used for 3D printing. Loading versatility allows for several different applications.

The implantable devices described herein are developed as a tool for delivering therapeutic agents with the most versatility possible while still retaining an overall simplicity that can be utilized in a practical fashion. This is important given the varied needs for delivery platforms in several fields. As such, both the method of fabrication and the overall design of the implantable device provides an extensive range of adaptability in several regards (FIG. 9). 3D printing enables structural versatility via alterations in dimensions, such as shape, size, thickness, and porosity. Additionally, 3D printing enables material versatility, including the possibility of utilizing biodegradable polymers or mixtures containing biodegradable polymers. This provides for greater possibilities of utilizing materials combined with therapeutic molecules for additional delivery options (for example, the outer wall of the device can be loaded with therapeutic agents that are released as the biodegradable polymer degrades). Finally, the implantable devices described herein have loading versatility. They can be filled with other technologies for controlled drug delivery to alter the release rate into the tissue. In this regard, the implantable devices can provide a regulated means of delivery control based on both the properties of the implantable device and the materials loaded therein. Furthermore, the implantable devices may improve outcomes from therapies that have had faced certain technical limitations, including stem cell and gene therapies. In these cases, inappropriate cellular activities and micro-environments have often limited the success of the therapy. Creating a protected, fixed, and conducive local environment within an implantable device may provide a means of making these therapies more realistic for patient use in the future.

Given the production method, the device itself may therefore be designed to the requirements of the situation or patient on-demand straight from printer-to-patient. It may be feasible to image the afflicted targeted region or tissue, fabricate a custom-made device based on these dimensions in a short time frame (for example, less than 1 hour), have its contents exactly customized according to the therapeutic needs of the patient, and directly delivered to the region of interest, all within a day.

Figure 14:
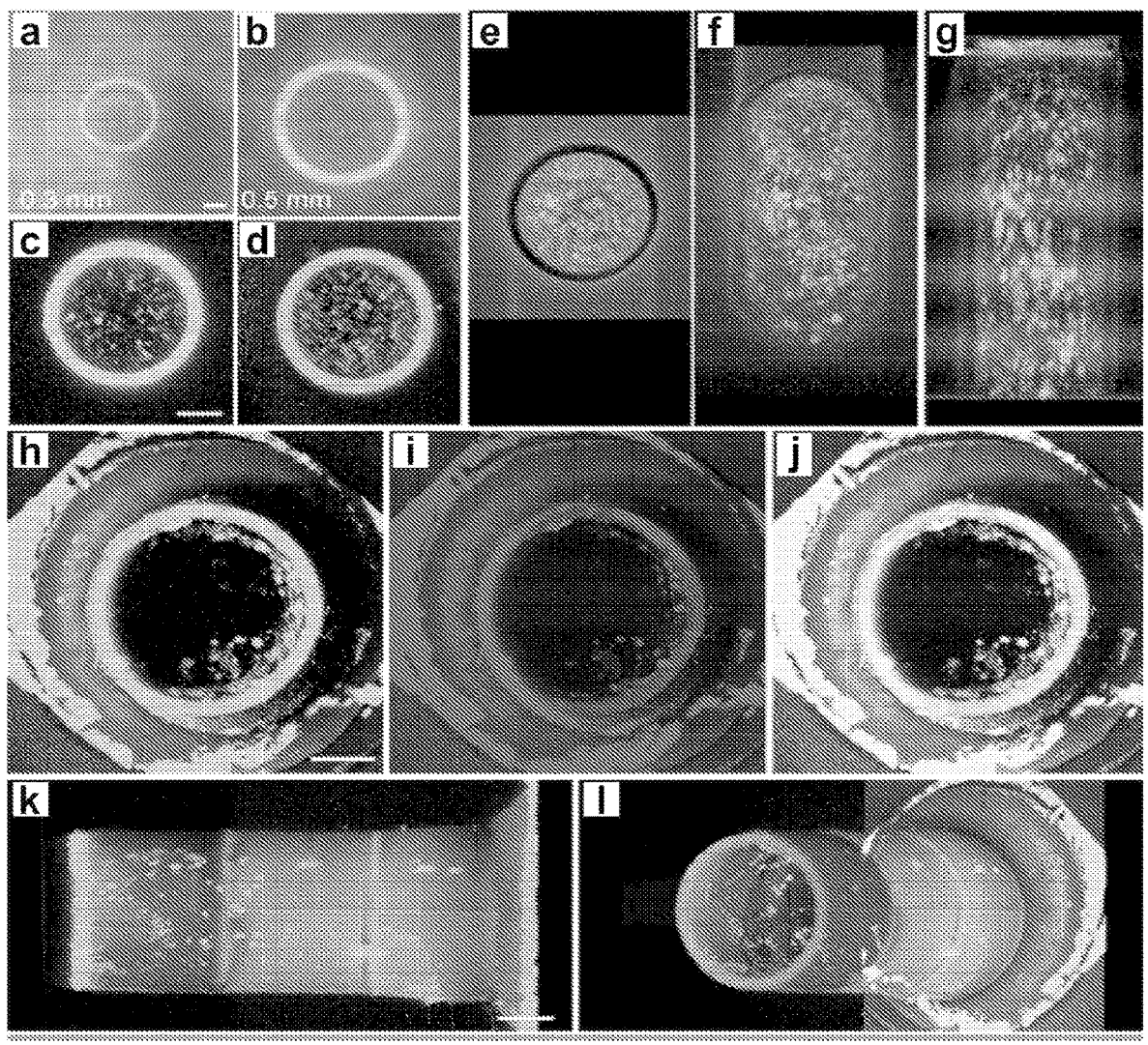
FIGS. 14A-14L show the results of human neural progenitor cell (hiNPC) culture and differentiation within implantable devices. (a) A 0.3 mm inner diameter and (b) a 0.5 mm inner diameter implantable device loaded with green fluorescent protein (GFP) positive hiNPCs (scale bar in a=100 micrometers). After 7 (c) and 21 (d) days in culture, hiNPCs within the implantable device show viability and growth (scale bar in c=100 micrometers). hiNPCs are viable and evenly distributed after 21 days, as evidenced by 3D representations of an implantable device showing the top view (e), oblique view (f), and side view (g).

Example 2: Culture and Differentiation of Human Neural Progenitor Cells (hiNPCs) within Implantable Devices In vitro differentiation. hiNPCs derived from induced pluripotent stem cells were suspended in Matrigel and inserted into implantable devices having inner diameters of 0.3 mm (FIG. 14A) and 0.5 mm (FIG. 14B). hiNPCs within the implantable devices grew and were viable over 7 day (FIG. 14C) and 21 day (FIG. 14D) culture periods. Three dimensional images of the hiNPCs after 21 days within the implantable devices show robust survival and even distribution throughout the device (top view: FIG. 14E, oblique view: FIG. 14F, side view: FIG. 14G). hiNPCs matured within the implantable devices when cultured under growth conditions for 7 days followed by 14 days of differentiation conditions. The cells cultured within the implantable device were positive for GFP (FIG. 14H) and for the neuronal maturation marker MAP2 (FIG. 14I). The merged image shows that GFP positive hiNPCs also stained for MAP2 (FIG. 14J). Neural processes extended within and along the surfaces of the implantable devices (FIGS. 14I-14J). Side (FIG. 14K) and oblique (FIG. 14L) views of an implantable device also show the localization of the differentiated cells throughout the device.

Figure 15:
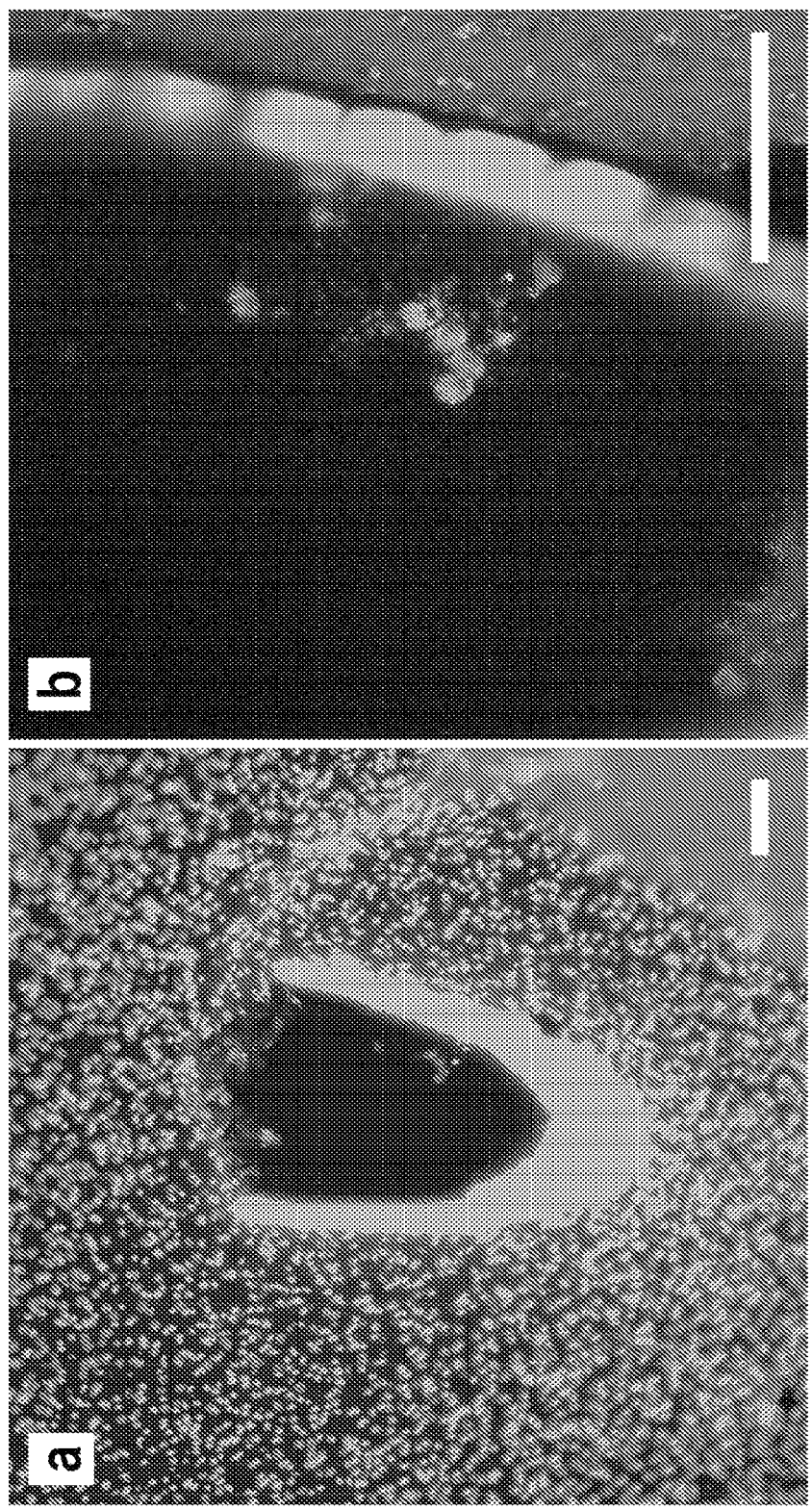
FIGS. 15A-15B shows that hiNPCs loaded in implantable devices maintain survival and display branching 1 month after implantation into the brain. (a) GFP positive hiNPCs are found within the implantable device 1 month after delivery to the adult mouse cortex. The inside of the implantable device has limited DAPI staining, indicating that surrounding cells did not infiltrate the device. (b) Higher magnification reveals branching structures from the GFP positive cells implanted via the implantable device.

In vivo implantation. GFP positive hiNPCs were resuspended in Matrigel and loaded into implantable devices. After the devices were capped with cyanoacrylate adhesive, they were implanted into the adult mouse cortex. Mice were sacrificed 1 month post-delivery. GFP positive cells were still located within the implantable device (FIG. 15A), but the relative lack of GFP negative cells that are positive for DAPI staining (such as that in the surrounding tissue) indicates that the cells from the surroundings did not infiltrate the device. Higher magnification shows branch structures from these cells (FIG. 15B).

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claim

What is claimed is:

1. An implantable device for housing one or more therapeutic agents, the device comprising;
    a porous outer wall defining an interior void, wherein the interior void is sealed by at least one end structure, and wherein the end structure comprises a different material than the porous outer wall;
    a carrier material and a first therapeutic agent housed inside the interior void;
    wherein the total volume of the implantable device is from about 40 nanoliters to about 10 microliters,
    wherein the porous outer wall comprises a biocompatible and/or biodegradable material, and
    wherein the porous outer wall comprises a two-photon polymerization (2PP)-compatible photoresist.

2. The implantable device of claim 1, wherein the porous outer wall is cylindrical in shape.

3. The implantable device of claim 2, wherein the diameter of the interior void is from 10 to 20 times greater than the thickness of the porous outer wall.

4. The implantable device of claim 1, wherein the thickness of the porous outer wall is from about 20 microns to about 10,000 microns.

5. The implantable device of claim 1, wherein the porous outer wall comprises pore openings, and wherein the pore openings have widths ranging from about 0.5 micrometers to about 25 micrometers.

6. The implantable device of claim 1, wherein the porous outer wall has a pore density of from 200 to 50,000 pores per millimeter squared.

7. The implantable device of claim 1, wherein the porous outer wall comprises poly(propylene fumarate) (PPF).

8. The implantable device of claim 1, wherein the porous outer wall is configured to be detected by imaging modalities.

9. The implantable device of claim 1, wherein the therapeutic agent is a cell or a cell-derived material.

10. The implantable device of claim 1, wherein the therapeutic agent is releasable via pore openings of the porous outer wall.

11. The implantable device of claim 10, wherein the therapeutic agent is a polynucleotide, a polypeptide, or a small molecule.

12. The implantable device of claim 10, wherein the therapeutic agent is a neuromodulatory agent.

13. The implantable device of claim 1, wherein the porous outer wall comprises a second therapeutic agent.

14. The implantable device of claim 1, wherein the carrier material is agarose.

* * * * *